(12) United States Patent
Davis et al.

(10) Patent No.: US 8,323,208 B2
(45) Date of Patent: Dec. 4, 2012

(54) NEUROLOGIC MONITORING SYSTEM AND METHOD

(76) Inventors: Timothy Taylor Davis, Santa Monica, CA (US); Hyun Woo Bae, Santa Monica, CA (US)

(*) Notice: Subject to any disclaimer, the term of this patent is extended or adjusted under 35 U.S.C. 154(b) by 0 days.

(21) Appl. No.: 12/775,171

(22) Filed: May 6, 2010

(65) Prior Publication Data

US 2010/0286554 A1    Nov. 11, 2010

Related U.S. Application Data

(60) Provisional application No. 61/286,703, filed on Dec. 15, 2009, provisional application No. 61/177,181, filed on May 11, 2009.

(51) Int. Cl.
*A61B 5/04* (2006.01)

(52) U.S. Cl. .................................. 600/554; 600/546

(58) Field of Classification Search .................. 600/546, 600/554; 606/41, 42
See application file for complete search history.

(56) References Cited

U.S. PATENT DOCUMENTS

| 4,159,022 | A | 6/1979 | Pevsner |
| 5,452,719 | A | 9/1995 | Eisman |
| 6,466,817 | B1 | 10/2002 | Kaula |
| 6,569,161 | B2 | 5/2003 | Zappala |
| 6,640,121 | B1 | 10/2003 | Telischi |
| 2003/0045808 | A1 | 3/2003 | Kaula |
| 2003/0088185 | A1* | 5/2003 | Prass ............................ 600/546 |
| 2003/0105503 | A1 | 6/2003 | Marino |
| 2004/0097801 | A1 | 5/2004 | Mesallum |
| 2004/0199084 | A1 | 10/2004 | Kelleher |
| 2004/0225228 | A1 | 11/2004 | Ferree |
| 2005/0085743 | A1* | 4/2005 | Hacker et al. ................. 600/554 |
| 2005/0149035 | A1 | 7/2005 | Pimenta |
| 2005/0182454 | A1 | 8/2005 | Gharib |
| 2006/0025703 | A1 | 2/2006 | Miles |
| 2007/0016097 | A1 | 1/2007 | Farquhar |
| 2007/0021682 | A1 | 1/2007 | Gharib |
| 2007/0149892 | A1* | 6/2007 | Guldalian ..................... 600/554 |
| 2007/0208227 | A1 | 9/2007 | Smith |
| 2008/0064976 | A1 | 3/2008 | Kelleher |
| 2008/0064977 | A1* | 3/2008 | Kelleher et al. ............... 600/546 |
| 2008/0065178 | A1 | 3/2008 | Kelleher |
| 2008/0214953 | A1 | 9/2008 | Hashimshony |

OTHER PUBLICATIONS

International Search Report and Written Opinion of the International Searching Authority mailed Dec. 16, 2010, in corresponding International Patent Application No. PCT/US2010/033913, filed May 6, 2010, 7 pages.

(Continued)

*Primary Examiner* — Jeffrey G Hoekstra
(74) *Attorney, Agent, or Firm* — Christensen O'Connor Johnson Kindness PLLC

(57) ABSTRACT

A method, system, and products that allow for accurate localization, virtual depiction, and testing of nerve(s) or neural structures that course through or around a proposed surgical site are described. The method and system employs a variety of types of neurodiagnostic tests that incorporate sensory, motor, and mixed nerve conduction studies in an orthodromic and antidromic fashion as well as utilizing triggered electromyography. This method, system, and products allow for a much more specific and sensitive method to assess the baseline function and continued integrity of nerves and neural structures prior to, during, and after a surgical procedure.

18 Claims, 21 Drawing Sheets

OTHER PUBLICATIONS

Bergey, D.L, et al., "Endoscopic Lateral Transpsoas Approach to the Lumbar Spine: Discussion," from Spine 29(15), Aug. 2004, <http://www.medscape.com/viewarticle/487929_4...> [retrieved Mar. 23, 2009], 4 pages.

"Cascade®," Cadwell Laboratories, Inc., Kennewick, Wash., PN# 100820-937, Rev. 4, 2008, 5-page brochure.

"Sierra® Wave® emg/ncv," Cadwell Laboratories, Inc., Kennewick, Wash., PN# 100813-937, Rev. 4, 2008, 12-page brochure.

* cited by examiner

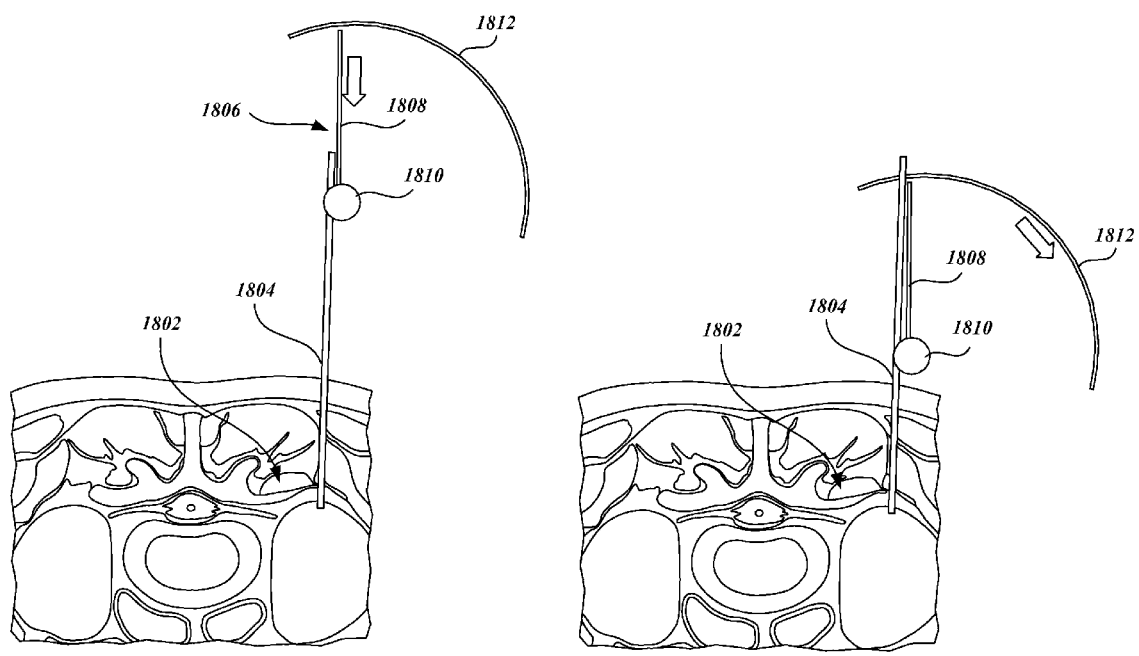
*Fig.18A.*  *Fig.18B.*

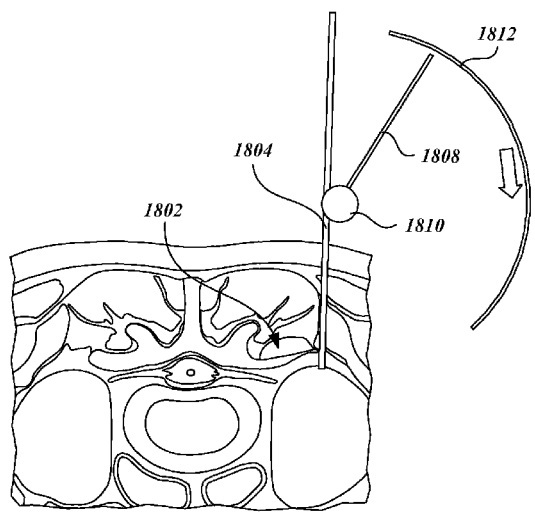
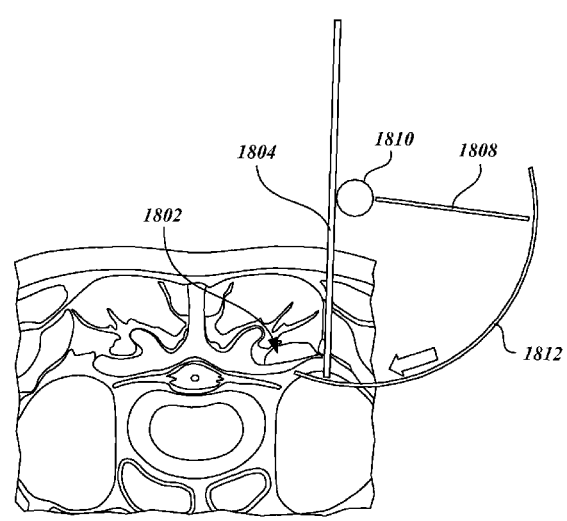
*Fig.18C.*  *Fig.18D.*

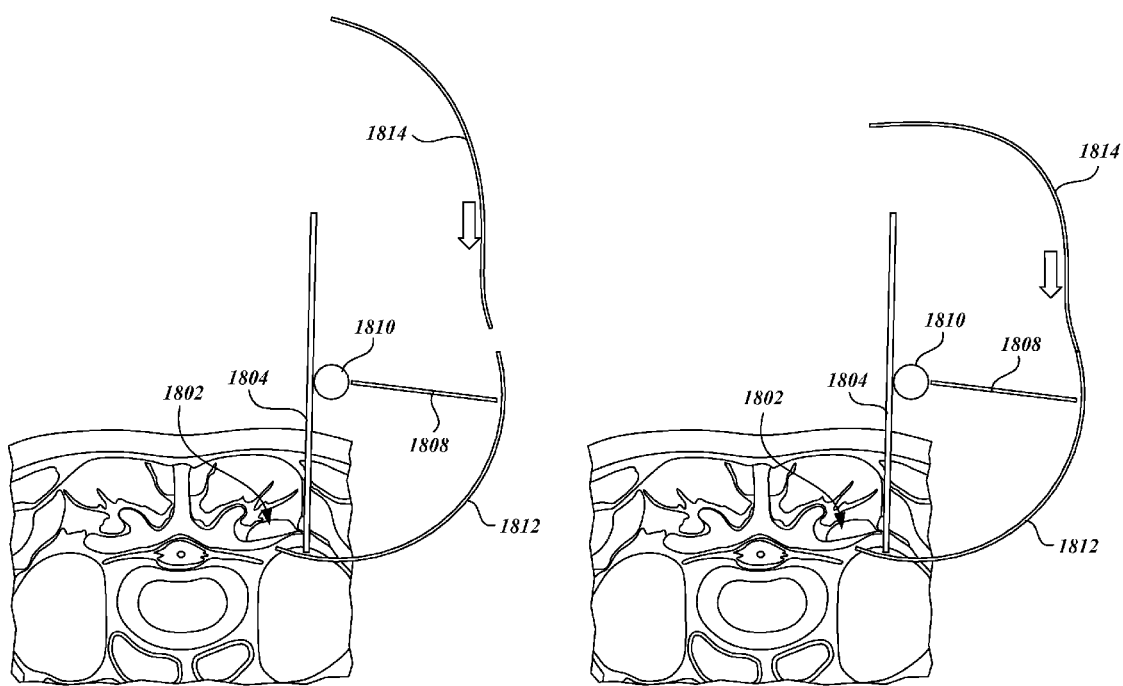
*Fig.18E.* *Fig.18F.*

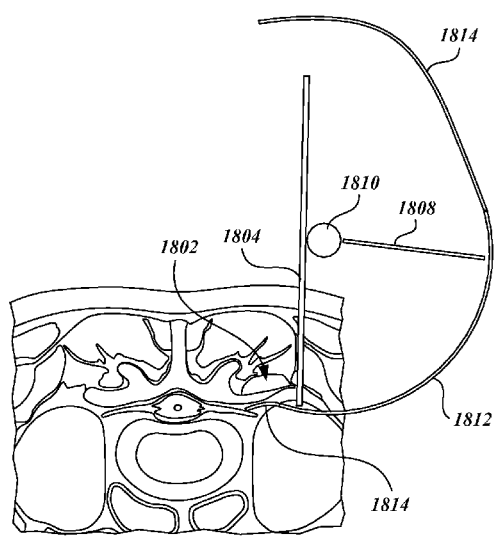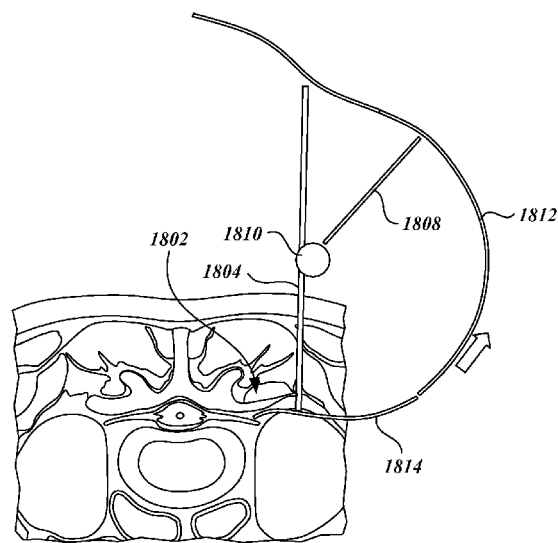
*Fig.18G.*          *Fig.18H.*

NEUROLOGIC MONITORING SYSTEM AND METHOD

CROSS-REFERENCES TO RELATED APPLICATIONS

This application claims the benefit of U.S. Provisional Application No. 61/286,703, filed Dec. 15, 2009, and the benefit of U.S. Provisional Application No. 61/177,181, filed May 11, 2009, both applications being expressly incorporated herein by reference.

BACKGROUND

Surgery, particularly minimally invasive surgery, often requires the use of retractors. A retractor is a medical instrument that, when inserted in an incision or opening in the body, is used to separate tissue to permit better visualization and access to the underlying target of the surgery. Retractors will oftentimes expand an initial skin incision to more than twice the original size and cause compression to the surrounding tissue (neural, vascular, and other soft tissue structures) in the process. Minimally invasive surgery offers the advantages of decreased trauma, less post-operative pain, faster recovery, and a smaller surgical scar. Yet studies have shown that the learning curve for minimally invasive surgical techniques can be steep for even an experienced spine surgeon. This leaves the possibility of complications and unnecessarily long surgeries during the learning phase prior to the development of an efficient technique. A minimally invasive procedure will normally require a specialized retractor. These specialized retractors allow good visualization of the target tissue but, due to the small incision, do not allow adequate visualization of the surrounding structures. It is known that excessive compression or traction on neural structures as a result of using a retractor may result in damage and permanent loss of nerve function, which translates into pain, numbness, and weakness post-operatively.

In lateral access spine surgery, an incision is made in the flank and dissection is performed through the retroperitoneal space and then through the psoas muscle to allow access to the spinal column. A retractor is advanced through this same tract and then expanded in the psoas muscle, revealing the spinal column. The psoas muscle is traversed by the lumbar plexus (the neural bundle that supplies the leg), and anatomic and clinical studies have shown that branches of the lumbar plexus are in potential jeopardy during a transpsoas spinal approach. Patients undergoing lateral access transpsoas spine surgery have been reported to have neural deficits post-operatively thirty percent of the time. It is therefore necessary to identify contact and subsequent compression or damage of a nerve(s) as it occurs during placement and expansion of the retractor and throughout the course of a lateral access surgery in the spine. Current intraoperative neuromonitoring systems allow for testing of neural structures using a medical instrument that is used in performance of the surgery. U.S. Patent Application Publication No. 2005/0182454 discloses, for example, a surgical system for electrically stimulating nerves via one or more stimulation electrodes at the distal end of surgical access components while monitoring the EMG responses of the muscle groups innervated by the nerves. This is accomplished via 8 pairs of EMG electrodes placed on the skin over the major muscle groups on the legs. U.S. Pat. No. 6,466,817 discloses a system for detecting proximity to a nerve and status of a nerve by providing a stimulus to a calibration electrode and a proximity electrode. The system includes EMG electrodes to receive the response after a stimulus is applied to the calibration or proximity electrode. The calibration electrode is positioned near a nerve. The proximity electrode may be coupled to any medical device including a cannula, needle, catheter, ablation device, laser, etc.

The above types of tests often give non-specific neurodiagnostic changes during a surgery, which can be open to interpretation. A neural pathway will conduct electrical impulses from one end to the other whether created internally by the patient or created externally by a method of neuromonitoring. The signals can further degrade over increased lengths of a given pathway and as the signals cross a synapse (nerve-nerve interface).

In contrast to prior art methods, the disclosed method and apparatus include testing shorter segments of a neural pathway and, in contrast to providing stimulation from a medical device/electrode at the surgical site, the disclosed method tests specifically, across a site of suspected injury or surgical site, such as proximal to distal and vice versa. A shorter neural segment will give a more reproducible reliable response.

SUMMARY

The present invention includes a system, products, and related methods for identifying the location and testing the performance of neural structures prior to surgery and protecting neural structures during surgical procedures by detecting changes in performance of the neural structures as they develop. Monitoring nerve and nerve root for functional integrity or detecting injury during a surgical procedure is disclosed by means of measuring neural function of a segment of nerve that spans from a location proximal of the surgical site to distal of the surgical site that is the potential site of injury. This is performed prior to surgery in order to obtain a "baseline" of normal neural function and is performed multiple times and in opposing directions during the procedure in order to verify continued normal neural function or deterioration of function across the surgical site.

Disclosed is a neurodiagnostic system, which includes a control unit, internally placed probes/electrodes in the patient, combination slave boxes capable of both sending a stimulus to a probe/electrode as well as receiving a signal from a recording probe(s)/electrode(s), and a localization probe designed to send a stimulus in order to detect neural structures during insertion to a potential surgical site. The control unit consists of hardware, software, and firmware, which has the capability of delivering a stimulus as well as receiving a signal from recording electrodes on or in the patient, converting this analog signal into digital format and then into waveforms. The control unit is also capable of identifying the relationship of a stimulus applied and a waveform produced. The control unit and software is capable of performing analysis of the waveforms and calculating conduction velocities, elapsed times between stimulus and responses, latencies, amplitudes, conduction velocity, or area of compound action potential, and any combination or calculation using these values. Baseline waveforms are stored and compared to future testing of the same neural structure in order to detect changes in neural function during a surgical procedure. The waveforms that are produced are projected on a display screen on the control unit as well as to a screen that the surgeon performing the surgery can visualize. The control unit display can also be visualized by a remote supervisor via a digital communication cable such as a CAT 5, Ethernet line, or any other variant of communication cable connected to a network of any kind that stores, communicates, or moves digital information.

In another aspect, a probe/electrode and method of inserting the probe are provided that allow access to a point of the nerve that has not been previously accessible due to the deep course of the nerve through bone, muscle, and soft tissue structures. The probe allows testing to be performed at a location deep inside the body and proximal or distal to a surgical site. This function cannot be performed using a "conventional" electromyography needle that is currently on the market. The current needles are limited in length and are not designed to bend. They also have a hub at the surface end that would be easily bumped during surgery and pierce the nerve during surgery. The disclosed probe/electrode is long enough to enable tip proximity to the nerve or neural structures in any patient regardless of the body habitus (size, girth of the patient) or depth of the nerve course. Once the probe is in place, it can then be bent to become flush with the surface of the skin to ensure that the probe will not penetrate any deeper than the desired placement. With current electromyography needles, the length of the proximal portion of the needle cannot be modified from patient to patient. Therefore, in a slender patient, there may be a portion of the needle that is still exposed outside of the skin and if bumped during the surgical procedure would impale the nerve or neural structure to which it was adjacent. The disclosed probe has a blunt tip. The disclosed probe can be located deep in the tissue using an introducer needle with the aid of imaging technology, such as fluoroscopy, CAT scan, and ultrasonic means, for example. In another embodiment, the probe is sharp, and the connection to the electrode wire is of minimal diameter, and the probe can still be bent to a flush level with the skin. In this embodiment, there is no need for the introducer needle.

In a further embodiment, the system uses a combination slave box. The combination slave box is connected to the control unit and is manipulated by a technician via a manual switch in one embodiment of the system or via a remote electronic switch at the control unit in another embodiment of the system. This slave box has the capability of sending a stimulus through a specific probe(s)/electrode(s) during one form of testing and then switching function in order to work as an amplifier receiving a signal from a recording probe(s)/electrode(s). For example, the slave box enables the same probe to be used for both sending a stimulus in one test, and receiving a signal in another test with the same probe. This advantageously avoids having to disconnect and reconnect probes for different tests.

In one embodiment, the system requires the technician to switch electrodes from the designated slave stimulus box to the designated amplifier box, and vice versa, during testing in order to perform the neurodiagnostic studies that volley signals from one location to another. These studies will be elaborated upon in the description section of this document.

In a further embodiment, a localization probe is disclosed that permits the localization of a neural structure. The localization probe may be used to localize the neural structure while a tract is made in the tissue where the retractor will later be placed. By using the localization probe to guide the surgeon around and away from the neural structure, the creation of the tract is accomplished with minimal injury to the neural structure. Furthermore, the tract will be created to avoid the neural structure so that when the retractor is used, the neural structure will not be in proximity to the retractor. In one embodiment, the localization probe is manually operated by the surgeon performing the surgery. This probe may or may not have a stimulus intensity dial that enables the surgeon to control the level of stimulus intensity delivered. This probe is rotated as it is inserted and a stimulus is sent in a unidirectional manner. The stimulus produces a signal that is conducted through a segment of nerve(s) or neural structure and delivered to recording probe(s)/electrode(s) at the nerve roots, the femoral nerve, and the muscles. These signals are routed through an amplifier slave box(es), carried to the control unit, calculations are made by the control unit using the depth at which the stimulus was delivered, the level of stimulus delivered, the angle/direction of stimulus, the location of the recording probe(s)/electrode(s), the intensity of the signal captured by the recording probe(s)/electrode(s), the elapsed time between stimulus and signal recording, and the known anatomy of the neural structures. Using these calculations, a three dimensional virtual image can be simulated and displayed with accuracy in regard to the proximity, direction, and depth from the skin of the nerve(s) or neural structure(s) that traverse through or around the surgical site.

In a further embodiment, the localization probe is the same as the aforementioned, but also has a motorized rotation that is synchronized with a repetitive stimulation as well as with the signals received by the recording electrodes.

In a further embodiment, the localization probe is the same as the aforementioned, but also has an automated depth gauge that is synchronized with the previous information and calculations.

In a further embodiment, an arc introducer apparatus is disclosed. The arc introducer apparatus includes: a rotating axis; a radius arm connected to the rotating axis, wherein the radius arm is configured to connect to an arc introducer needle; and wherein the arc introducer apparatus is configured to be inserted over a guidewire. The arc introducer apparatus can further include an arc introducer needle at one end of the radius arm.

In a further embodiment, a method for placing a neuromonitoring electrode within a tissue of a body includes placing a guidewire within a body to reach a deep tissue; inserting the radius introducer apparatus disclosed above over the guidewire to approximately be flush to a surface of the body; adjusting a radius arm of the radius introducer apparatus to a length approximately equal to the depth of the guidewire inside the body; pivoting the radius arm with the arc introducer needle to insert the arc introducer needle to reach a neural structure to be monitored; and inserting a flexible neuromonitoring electrode through the arc introducer needle, and removing the arc introducer needle to place the electrode at or close to the neural structure to be monitored.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 18A through 18H are diagrammatical illustrations of an apparatus and steps for a method to introduce a nerve probe/electrode to circumvent the posterior lateral fusion mass.

DETAILED DESCRIPTION

Figure 1:
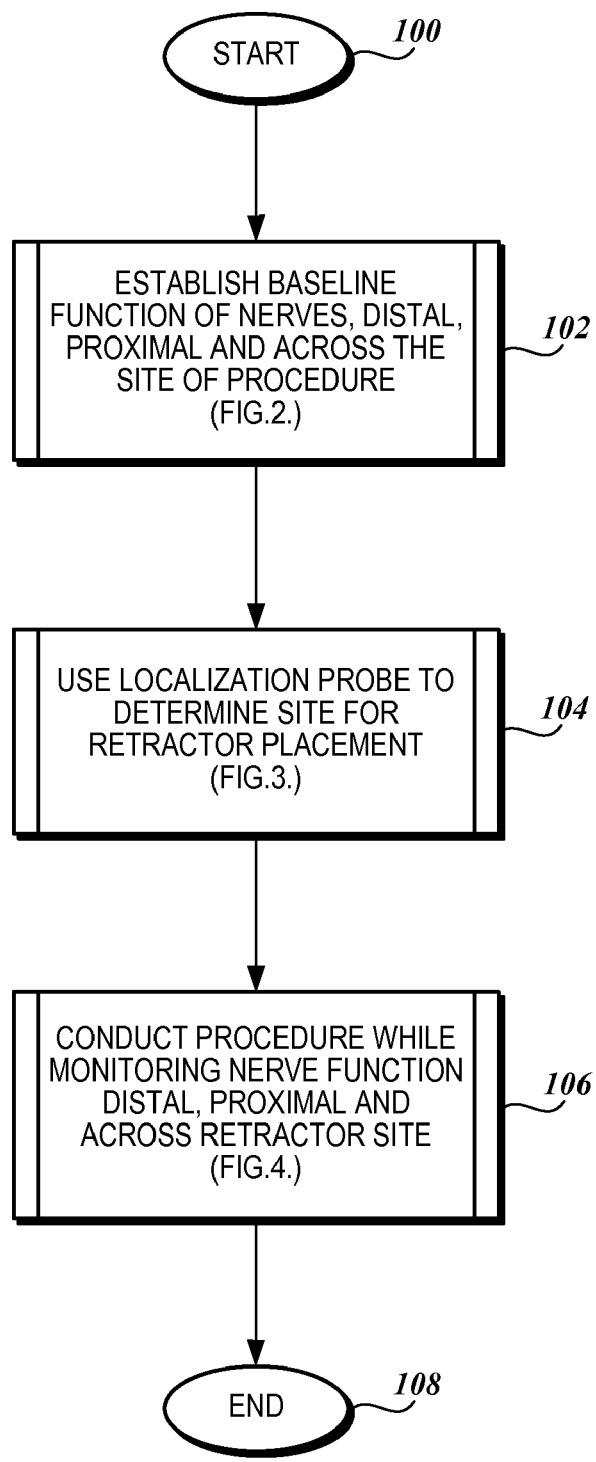
FIG. 1 is a flow diagram of one embodiment of a method for monitoring nerve function during a surgical procedure.

Referring to FIG. 1, one embodiment for a method of preparing for and monitoring nerve function during a surgical procedure is illustrated. Although the description and the figures may refer to a specific form of surgery, such as lateral access spinal surgery, the methods disclosed herein can be used in other types of surgery including, but not limited to, any minimally invasive procedure or an open surgery involving the use of medical instruments that in one way or another may apply traction or compression forces on nerves. Furthermore, the methods disclosed and claimed should not be construed as being limited to surgical procedures, as the methods disclosed and claimed herein relate to the monitoring of nerve function for other purposes. The methods disclosed herein provide for greater sensitivity in monitoring the nerve function during any surgical procedure, or otherwise, because the aim of the methods is to provide monitoring of more than one type of nerve fiber, including sensory and motor nerves and in more than one conduction direction. The methods disclosed herein allow for conducting monitoring of nerve function by testing the nerves both in an orthodromic as well as antidromic manner. Finally, the methods disclosed herein allow monitoring of nerve function by stimulating nerves at locations that are proximal to the surgical site and receiving the responses by nerves at locations distal to the surgical site, and vice versa, thus effectively testing for nerve signals across the surgical site in both directions.

Referring to FIG. 1, a method that includes preparing for and conducting monitoring of nerve function is illustrated. Block 102 is for establishing a baseline function of the nerves to be tested during the surgery. The method advantageously provides greater sensitivity to loss of nerve function by testing various types of nerve(s) fibers that are distal to the site of the procedure, proximal to the site of the procedure, and course across, through, or around the site of the procedure. The testing also includes orthodromic and antidromic testing. Orthodromic as used herein refers to testing an impulse propagating along an axon in the normal direction. Antidromic is testing propagation opposite to the ordinary direction that the nerve conducts. Block 102 is described in greater detail in association with FIG. 2.

Once a baseline function of nerves is established, the method moves to block 104. In block 104, a localization probe is used to determine the site for placement of a retractor. Although a retractor is disclosed herein as a medical instrument, the use of which will be monitored for its affect on nerve function, the methods and systems disclosed herein may be used to monitor other medical instruments that can be employed in any number of different surgical procedures, such as catheters, endoscopes, etc. Further, step 104 may be optional if the surgical procedure does not call for a retractor or similar instrument. When performed, the purpose of block 104 is to determine the path for the placement of a medical instrument, such as the retractor, to be used in the surgical procedure. A localization probe, described in greater detail below, is used to determine the location of any nerves to avoid damaging these nerves when placing the retractor. Block 104 is described in greater detail in association with FIG. 3.

After completion of block 104, the method enters block 106. In block 106, a surgical procedure can be performed. While nerve function monitoring during surgery is one object disclosed herein, the nerve conduction studies and the manner and order of conducting nerve conduction studies may be used for purposes other than surgery. The electrodes that are used in this block can be the same electrodes that were used in block 102. Since the electrodes used in block 102 were used to establish a baseline function of nerves, in order to determine whether the nerves undergo loss of function during surgery, the same nerves can be tested during the surgical procedure. The electrodes disclosed herein can have a dual purpose. For example, one test may use an electrode for nerve stimulation. The same electrode that is used for nerve stimulation in one test can also be used to record the response of the nerve in a different test, such as when testing calls for orthodromic and antidromic testing, or when conducting proximal to distal locations, or vice versa, regardless of whether the conduction is antidromic. Block 106 is described in greater detail in association with FIG. 4A.

Figure 2:
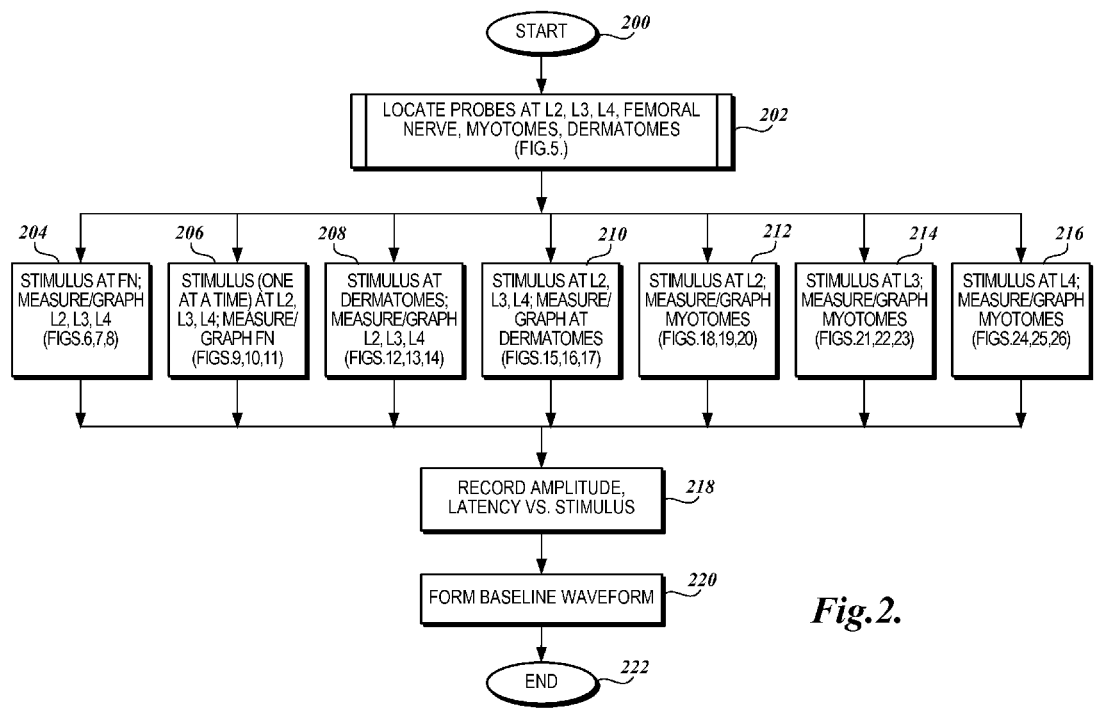
FIG. 2 is a flow diagram of one embodiment of a method for establishing a baseline function of nerves, including distal, proximal, and across the site of the procedure.

Referring to FIG. 2 now, which corresponds to a more detailed description of the block 102 of FIG. 1, a flow diagram for establishing the nerve function baseline is illustrated. The patient on whom the surgical procedure is to be performed is positioned as in the actual surgery. Preferably, the patient will be under general anesthesia. From the start block 200, the method enters block 202. Block 202 is for placing the probes in tissues within the patient. A probe, as used herein, is an electrical conductor that may be used to both deliver an electrical signal and/or receive an electrical signal. As such, the probe may also be referred to as an electrode when performing in that capacity. A suitable probe for this purpose is disclosed below. In one embodiment, the probe locations for a lateral transpsoas approach to the lumbar region of the spinal column are disclosed. However, the nerves to be monitored for other surgical procedures will become apparent to those skilled in the art from this disclosure. A purpose of the methods disclosed herein are to locate probes at locations that are proximal and distal to a surgical wound. In this manner, the nerves that pass, course through, or are proximal to a surgical wound and distal to a surgical wound can be monitored, orthodromically and antidromically, and effectively across the surgical wound. The disclosed method further provides for monitoring various types of nerve fibers, such as sensory nerves and motor nerves. The disclosed method advantageously provides greater sensitivity to better inform the physician of potential nerve damage.

One embodiment for monitoring nerve function for a lateral transpsoas approach to the lumbar region of the spinal column includes locating probes at one or any combination of nerve roots. For the lateral transpsoas approach surgery, the L2, L3, and L4 nerves are considered to be proximal nerves. Proximal, as used herein, refers to one of two positions that is the nearest to the spinal cord or brain as compared to another or other positions. Distal, as used herein, refers to a position that is further on the nerve path as compared to the proximal position. The nerve root as used herein is that portion of the nerve that exits the neuroforamen. The probes can be placed close to the nerve root or nerve and are placed with the aid of fluoroscopic localization as described in greater detail below. For purposes of describing an exemplary lateral transpsoas approach, the probes that are located at one or a combination of the L2, L3, and L4 nerve roots are proximal to the surgical site. A electrode/probe is also placed at the femoral nerve that is distal to the surgical site. Finally, electrodes/probes are placed at the L2, L3, and L4 myotomes and dermatomes that are also distal to the surgical site. Myotomes and dermatomes that correspond to the L2, L3, and L4 nerve roots are apparent to those of skill in the art. Areas of the body corresponding to the L2, L3, and L4 myotomes and dermatomes are well known from the literature. While specific nerves are disclosed herein as being monitored during lateral transpsoas spinal access surgery, any nerves and nerve roots in the body could be accessed using the disclosed probe. It is apparent that different surgical locations would call for placement of probes at different locations. Monitoring the nerve roots L2, L3, and L4 are merely representative of a procedure that includes traversing the psoas muscle. In other surgical procedures, other nerve roots may be selected. In this particular description, the L2, L3, and L4 nerve roots are chosen because they combine to form the femoral nerve in proximity to the psoas muscle in the lumbar spine. Therefore, these specific nerve roots and femoral nerve are consistently in jeopardy during a direct lateral transpsoas surgical approach. Monitoring sensory and motor nerves, proximal and distal, and across the surgical site can be applied to any nerve roots or nerves throughout the nervous system for providing greater sensitivity to loss of nerve function.

Figure 5:
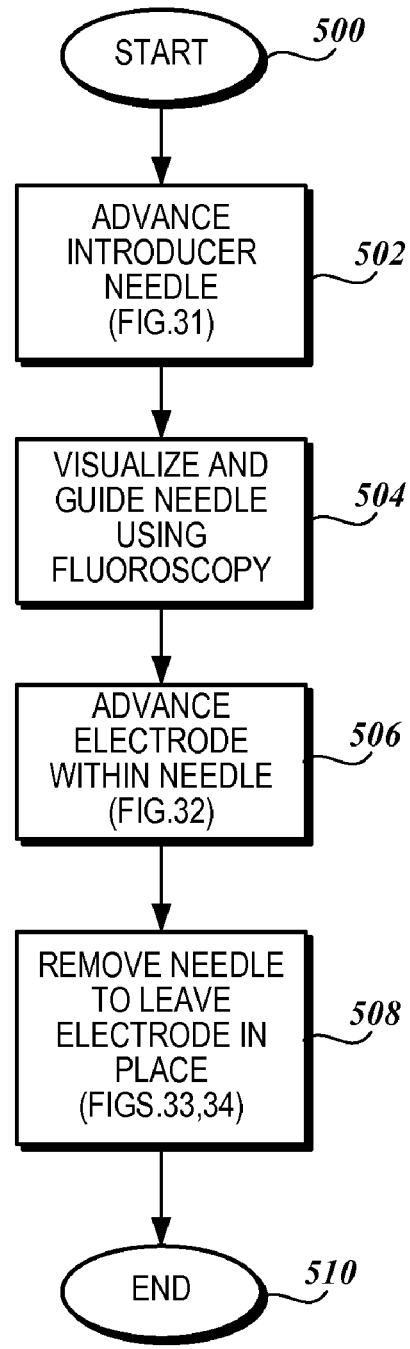
FIG. 5 is a flow diagram of one embodiment of a method for locating an electrode within a region of the body.

A procedure of the insertion of probes into the tissues to reach or be in proximity to monitor the various nerves will now be described in more detail in association with FIG. 5. This procedure can be used to introduce probes into nerves that course deep. The method of introducing probes into tissues is similar to the well-known Seldinger Technique. The Seldinger Technique is used for insertion of catheters to various hollow organs or blood vessels. However, to date, a Seldinger-like technique is not known for insertion of electrode probes for conducting nerve monitoring. Turning to FIG. 5, in block 502 a hollow introducer needle is advanced in the tissue. The introducer needle is a well known medical instrument. One embodiment of an introducer needle, for example, may be variable gauge and variable length. From block 502, the method enters block 504. In block 504, the method involves the use of fluoroscopy to enable the physician to visualize and be able to guide the introducer needle through the soft tissue to reach the nerve of interest. Alternatively, CAT scan, ultrasonic, or other suitable imaging technology may be used. From block 504, the method enters block 506. In block 506, once the introducer needle has reached the desired location, the physician advances the probe within the introducer needle to reach the desired depth. From block 506, the method enters block 508. In block 508, the physician removes the introducer needle to leave the electrode in place at one of the nerve root sites mentioned above, or otherwise at any other nerve. Alternatively, in another embodiment for inserting a probe, a radius trajectory apparatus could be used. FIGS. 18A to 18H show an apparatus and steps used in an alternative method for introducing a nerve probe/electrode. In one embodiment of FIGS. 18A through 18H, a radius introducer apparatus, as described herein, can be used to circumvent the posterior lateral fusion mass 1802. However, the disclosed apparatus and method can be used to circumvent other nerves. This apparatus and method is useful for avoiding certain neural structures during probe placement by use of a flexible probe. Avoiding certain neural structures is desirable to reach a target nerve, which the probe is intended to monitor or to provide a stimulus. FIG. 18A illustrates an introducer guidewire 1804 is placed from a direct posterior fluoroscopic approach to a position, which is lateral to a posterior lateral fusion mass 1802 and inferior to the tip of the transverse process. The tip of the guidewire 1804 is advanced in a lateral fluoroscopic view until the tip is at the dorsal aspect of the neuroforamen. A radius trajectory apparatus or radius introducer apparatus 1806 as disclosed herein includes a radius arm 1808 that may be adjusted to change the length. The radius arm 1808 is connected to a rotating axis 1810 at one end of the radius arm 1808. The opposite end of the radius arm 1808 is configured to hold an arc introducer needle 1812. The radius arm 1808 may be adjusted in length by telescoping pieces or the connection to the rotating axis 1810, or the arc introducer needle 1812 may be moved up or down on the radius arm to change the length from the rotating axis 1810 to the arc introducer needle 1812. An arc introducer needle 1812 is similar to an introducer needle; however, the arc introducer needle 1812 is shaped to provide a certain radius of curvature. This allows a flexible probe to be placed from a direction other than a direct linear approach. In one embodiment, the radius arm 1808 can be rigid and essentially linear and the arc introducer needle 1812 is rigid and has a radius of curvature. To attach the radius arm 1808 to the rotating axis 1810 or to the arc introducer needle 1812, either the radius arm 1808, the rotating axis 1810 or the arc introducer needle 1812 may have a clamping device. For example, the end of the radius arm 1808 can be inserted within a socket or a collar of the rotating axis 1810 composed of two halves, which can then be tightened around the radius arm 1808 to hold the radius arm through friction. To attach the arc introducer needle 1812 to the radius arm 1808, the clamp may be on the end of the radius arm 1808 and the arc introducer needle 1812 slides within two halves of the clamp, which is then tightened around the arc introducer needle 1812. The radius introducer apparatus 1806 is inserted over the guidewire 1804 at the rotating axis 1810 until flush with the skin as seen in FIG. 18B. The introducer guidewire 1804 has markings to indicate depth. The depth marker at the skin is noted and the radius arm 1808 is adjusted to the same length as also seen in FIG. 18B. FIGS. 18C and 18D illustrate the arc needle introducer 1812 is then pivoted in an arc as dictated by the length of the radius arm 1808 and inserted in the body until the tip is at the end of the guidewire 1804. In FIGS. 18E to 18H, the flexible probe/electrode 1814 is being introduced through the arc introducer needle 1812, requiring that the stylet or needle 1812 be removed so that the probe/electrode 1814 is placed through the arc introducer needle 1812 until the tip of the probe/electrode 1814 can be seen protruding medial to the lateral border of the fusion mass 1802, as seen in FIG. 18G. FIG. 18H shows the arc introducer needle 1812 being removed leaving the probe/electrode 1814 adjacent to the nerve to be monitored/stimulated. This method is made possible with the use of the probe disclosed herein, which is flexible and can be inserted through a curved introducer needle 1812.

Once the introducer needle is removed, the probe can be fixed to the patient, for example, with surgical tape and/or bending the probe to allowing the probe to lie close to the skin of the patient before taping to the skin. For that purpose, disclosed herein is a bendable, flexible probe. Probes can be placed at L2, L3, L4 nerve roots and the femoral nerve as disclosed above. Procedures for the placement of probes and the types of probes used at the myotomes and dermatomes are apparent to those of skill in the art and will not be described herein for brevity.

Returning to FIG. 2, once the probes are located at the L2, L3, and L4 nerve roots, the femoral nerve, and the selected myotomes and dermatomes, the method enters from block 202 into one or more blocks selected from 204, 206, 208, 210, 212, 214, and 216, simultaneously, in series, or randomly. Blocks 204 through 216 are representative of various nerve function monitoring schemes. It is to be understood that other monitoring schemes can be used, the ones described herein being merely exemplary. The disclosed method uses a number of electrodiagnostic modalities that can be used individually or in any combination in order simultaneously or randomly to assess neurologic integrity across a segment of nerve or nerves, prior to and during a surgical procedure. Furthermore, this method describes the testing of sensory, motor, and mixed fiber nerves in an orthodromic and antidromic fashion as well as triggered electromyography as a means of evaluating nerve integrity and performance. At least one nerve conduction study or EMG in a direction from proximal to distal and one nerve conduction study from distal to proximal are performed. The nerve function monitoring schemes will now be described.

Block 204 provides a method of measuring and/or graphing an orthodromic sensory nerve conduction study with a stimulus distal at the femoral nerve, conducting to proximal at the nerve root probe/electrode recording site. This step produces a "baseline" performance for this anatomic section of the sensory nerve fibers for the patient. This nerve conduction study is then repeated in later steps, when during the actual surgery, a surgical retractor is in use at a location between the stimulus site and the recording site, in order to identify damage to the nerve fibers as compression, traction, or vascular compromise occurs.

Block 206 provides a method of measuring and/or graphing a mixed (sensory and motor) nerve conduction study with a stimulus provided proximal at a nerve root probe, one probe at a time, conducting to distal at the femoral nerve recording site. This step produces a "baseline" performance for this anatomic section of the sensory and motor nerve fibers for the patient. This will produce a distinct unique waveform for each nerve root stimulated. These nerve conduction studies are then repeated in later steps when, during the actual surgery, a surgical retractor is in use at a location between the stimulus site and the recording site in order to identify damage to the nerve fibers as compression, traction, or vascular compromise occurs.

Block 208 provides a method of measuring and/or graphing an orthodromic sensory nerve conduction study with a stimulus distal at the dermatome locations, conducting to proximal at the nerve root probe recording site. This step produces a "baseline" performance for this anatomic section of the sensory nerve fibers for the patient. This nerve conduction study is then repeated in later steps when, during the actual surgery, a surgical retractor is in use at a location between the stimulus site and the recording site in order to identify damage to the nerve fibers as compression, traction, or vascular compromise occurs.

Block 210 provides a method of measuring and/or graphing an antidromic sensory nerve conduction study with a stimulus provided proximal at the nerve root probe/electrode, one probe at a time, conducting to distal at the dermatome recording site. This step produces a "baseline" performance for this anatomic section of the sensory nerve fibers for the patient. This will produce a distinct unique waveform for each nerve root stimulated. These nerve conduction studies are then repeated in later steps, when, during the actual surgery, a surgical retractor is in use at a location between the stimulus site and the recording site in order to identify damage to the nerve fibers as compression, traction, or vascular compromise occurs.

Blocks 212-214 provide a method of measuring and/or graphing a triggered electromyographic response to a stimulus provided proximal at the nerve root probe, one probe at a time, conducting to distal at the myotome recording site that corresponds to the aforementioned nerve root, surface electrode, or needle electrode. This step produces a "baseline" performance for this anatomic section of the motor nerve fibers as well as the neuromuscular junction for the patient. This will produce a distinct unique waveform generated from the myotomes that correspond to each nerve root stimulated. These triggered electromyographic studies are then repeated in later steps when, during the actual surgery, a surgical retractor is in use at a location between the stimulus site and the recording site in order to identify damage to the nerve fibers as compression, traction, or vascular compromise occurs. In a situation where anesthetics negatively impact the neuromuscular junction, electromyographic testing, such as the one described in Blocks 212-216, may be unreliable. The disclosed method of testing overcomes this drawback by performing a variety of tests on more than one nerve.

Blocks 204-216 provide examples of electrodiagnostic testing for a segment of nerve or nerves. In each instance, a circuit is formed beginning with stimulus provided by a neuromonitoring machine that is sent a stimulator/amplifier box (slave box). The stimulator/amplifier box is connected to a stimulus probe, which applies the stimulus to a segment of the patient's nerve tissue or combination of nerve tissue and muscle tissue. The nerve reacts to the stimulus which is recorded at a remote nerve with a recording electrode. The signal received by the recording electrode is amplified by an amplifier circuit in the stimulator/amplifier box, processed by an analog to digital converter, and then sent back to the neuromonitoring machine, which can process the digital information into a waveform.

The electrical stimulus is generated at the neuromonitoring machine, with the intensity being controlled, such as by a technician under the instruction of a supervising physician. This stimulus is applied to one location in the patient's body through a stimulation probe, the electrical impulse that is generated is transmitted along the nerve fibers by depolarization in a specific direction towards a recording electrode, which receives the electrical impulse. The electrical impulse is then carried to an amplification circuit in the stimulator/amplifier box, which also filters out other background electrical signals and noise, by using a reference electrode. The remaining signal is then carried to the neuromonitoring machine where it is processed through an analog to digital converter to produce digital information that is converted into a waveform. The stimulus may be generated once or numerous times in order to generate a consistent reproducible waveform. Nerve sensory studies can oftentimes require hundreds of stimulations producing a single waveform for each stimulus. The neuromonitoring computer then averages the responses in order to produce a single waveform that is representative of those specific nerve fibers.

In block 218, for each electrodiagnostic modality, the stimulus intensity at which a consistent response at the recording electrode is generated is measured and documented and saved in memory, such as in the neuromonitoring machine. The waveform that is subsequently formed is also documented in a graph form as well as in terms of latency to onset or peak/trough and amplitude.

The information obtained by performing these electrodiagnostic studies in blocks 204-216 prior to any invasive surgical procedure produces a representative "baseline" neural function for the patient. Such baseline information can be stored in a memory of a neuromonitoring machine or other memory in one or more computing devices for future comparison.

In block 220, a baseline waveform can be created from the data for each testing scheme. The baseline waveform can be established with the patient under anesthesia, in a relaxed position (static state), with no limb manipulation (leg flexion/extension etc.) or surgical instrumentation in place other than for the probes. For each electrodiagnostic study performed, a stimulus is initiated at the control unit that is then sent to a stimulator/amplifier slave box, then through a probe/electrode to a specific point of the nerve(s) or neural structure in the patient. The signal is then carried along a section of the neural structure to the location of a recording probe(s)/electrode(s). The signal is then carried to a stimulator/amplifier slave box that also incorporates a reference electrode to decrease background electrical interference, "noise," and then the signal is carried back to the control unit where it is converted from an analog signal to a digital signal using an analog digital converter. The digital information is then plotted in a waveform, and the relationship between stimulus intensity and resultant waveform is identified using time to signal strength response and intensity of stimulus to size (amplitude) of signal response. A representative neuromonitoring machine capable of being used in the disclosed methods is the CASCADE system, provided by Cadwell Laboratories, Inc., of Kennewick, Wash., USA.

The baseline waveform creation routine ends in block 222. From block 222, the method returns to block 102 of FIG. 1 and enters the subroutine of block 104, which is described in more detail in association with FIG. 3.

Figure 3:
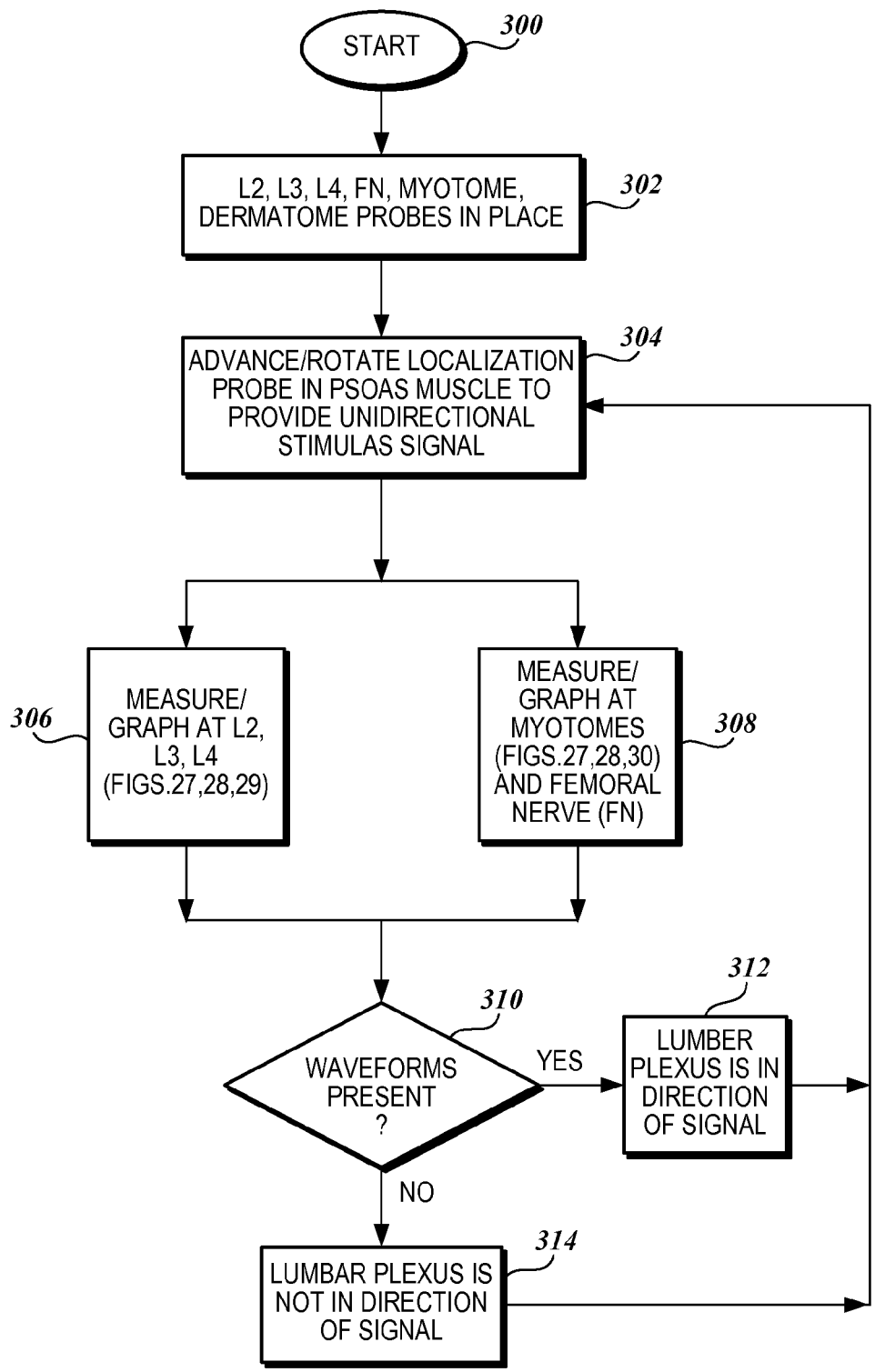
FIG. 3 is a flow diagram of one embodiment of a method for using a localization probe to determine the site for retractor placement.

Referring to FIG. 3, a flow diagram for localizing a nerve in a muscle tissue is illustrated. As used herein, "localizing" is intended to refer to a procedure for determining the location of any neural structure in proximity to a surgical would, such that once knowing its location, a medical instrument can be used safely and in a manner that can avoid touching or being in close proximity so as to avoid risk of injury to the nerve. For example, in lateral spinal surgery, an incision for inserting a retractor is made in the psoas muscle to gain access to a spinal column vertebra. In the case of performing a transpsoas approach, it is desirable to locate the lumbar plexus to allow for the safe introduction of a retractor. Nerves that can be identified during the plexus localization procedure include the genitofemoral nerve (L1, L2 roots) and lateral femoral cutaneous nerve (L2 L4), since these are in jeopardy during the transpsoas approach. It is to be understood that the localization of the lumbar plexus is specific to a transpsoas procedure. However, the invention is not thereby limited. In the case when a different surgical procedure is being performed, it would be apparent to those skilled in the art the nerve(s) or neural structures in proximity to the operative site that would need to be localized.

The method for localization of a nerve or neural structure begins in block 300. From block 300, the method enters block 302. Block 302 is to signify that the probes and/or electrodes at the nerve roots L2, L3, and L4, the femoral nerve, myotomes, and dermatomes are in place from the baseline waveform determination procedure discussed above in connection with FIG. 2. From block 302, the method enters block 304. In block 304, a localization probe is advanced in the psoas muscle. The localization probe is able to provide a unidirectional stimulus signal. A unidirectional signal is a signal that generally only travels in one direction, such that the signal is not spread across more than several degrees of a 360 degree arc. Accordingly, the localization probe can be rotated such that the potential area to be stimulated includes all 360 degrees of rotation. For such purpose, a localization probe that provides a unidirectional signal will be described in more detail below. The probe can further be rotated through 360 degrees to provide a signal in any direction. The probe is provided with a means for determining the direction of the unidirectional signal by reference to a constant reference point that allows the angle of rotation to be known when a signal is produced. The probe also has a depth gauge that is either manual or automated. The depth gauge provides a depth measurement at the time of unidirectional signal production. Thus, both the direction and the depth of the unidirectional signal can be determined. The probe rotation can also be under control of a neuromonitoring machine, described in more detail below. Thus, when a signal is applied using the localization probe, the depth and direction are known for any stimulus signal. This provides the ability to be able to map neural structures in three dimensions.

From block 304, the method can enter one or both blocks 306 and 308. Block 306 is used to measure and/or graph the nerve function response, if any, at the nerve roots L2, L3, and L4 after a stimulus is generated from the localization probe. Block 308 is used to measure and/or graph the nerve function response, if any, at the myotomes after a stimulus is generated from the localization probe. The neuromonitoring machine used to record, measure, and process the response signal can be the same as the neuromonitoring machine disclosed in connection with FIG. 2.

From blocks 306 and 308, the method enters block 310. In block 310, a determination is made as to whether any waveforms are present from the responses recorded at the L2, L3, L4, and myotome electrodes. If the determination is NO, the method enters block 314, signifying that the nerve is not in the direction of the stimulus signal. If the determination is YES, a second determination is made as to whether the waveforms that are present are a low or a high level stimulation. Any waveform generally indicates that the lumbar plexus nerve is in the direction of the stimulus signal. Depending on whether a low or a high level waveform is detected can indicate the proximity of the nerve to the probe. Further, because various types of nerves are being tested, some types of nerve fibers will be stimulated, while others are not. All the waveforms with corresponding values for stimulus intensity, amplitude, latency, depth and any difference from the baseline waveform can be displayed on a terminal. The physician can view the display that conveys a virtual image of the nerve(s) or neural structures in relation to the localization probe as well as the depth at which the nerve(s) or neural structures were encountered. This allows a surgeon to decide whether to advance the localization probe further or rotate the probe in order to find a way through the psoas muscle without hitting the lumbar plexus nerve. During this portion of the procedure, the surgeon is performing sensory and motor nerve conduction studies and triggered electromyograph responses.

The method disclosed in FIG. 3 is a tool to enable the physician to navigate a path through the psoas muscle in which a medical instrument, such as a retractor, will be inserted. The method disclosed in FIG. 3 is useful to locate a nerve(s) or neural structure such as the lumbar plexus so as not to damage any neural tissue when the retractor is advanced and subsequently expanded.

After completion of the subroutine of FIG. 3, the system is ready to proceed to the surgical procedure. From block 104, the method enters block 106 of FIG. 1. Block 106 is the subroutine performed during a surgical procedure after the preparatory subroutines of blocks 102 and 104 have been completed. Block 106 is described in more detail in association with FIG. 4A.

Figure 4A:
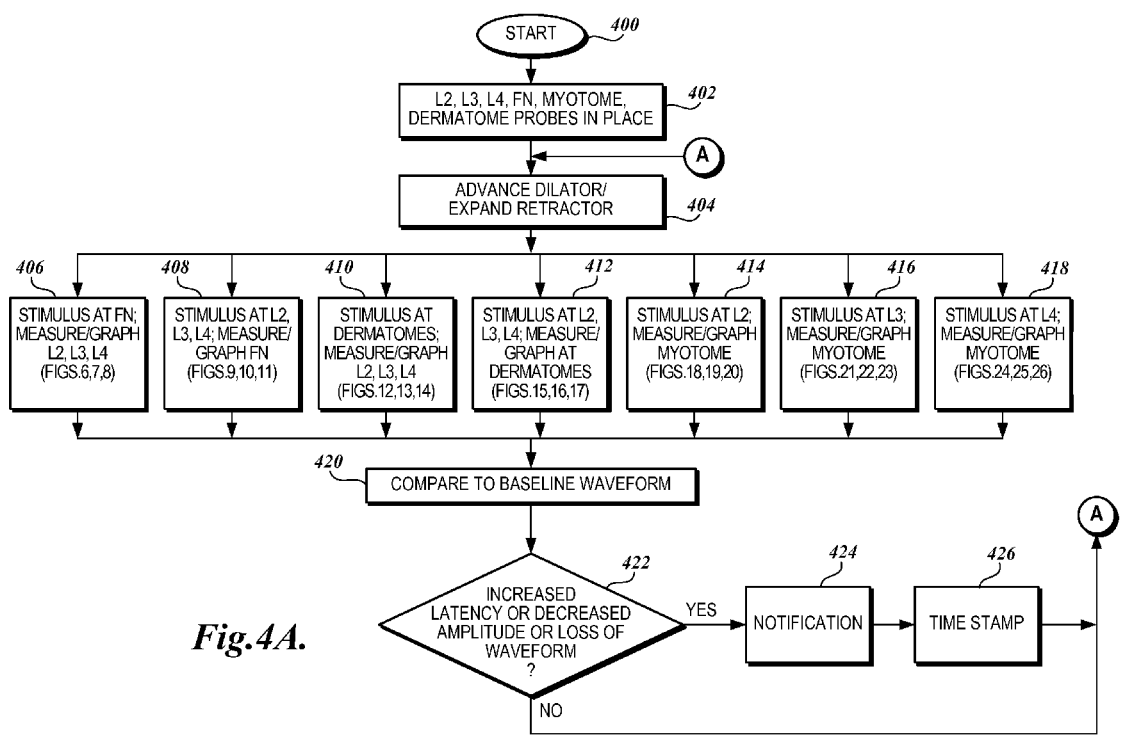
FIG. 4A is a flow diagram of one embodiment of a method for monitoring nerve function during a surgical procedure.
Figure 4B:
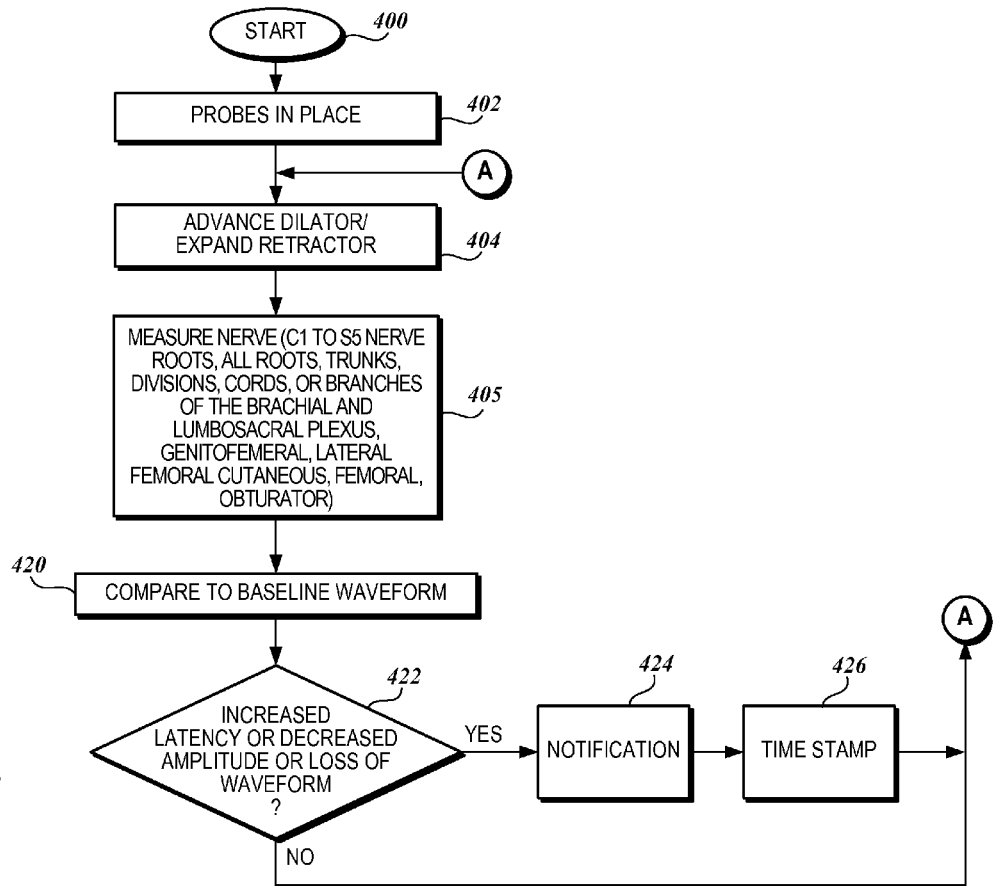
FIG. 4B is a flow diagram of one embodiment of a method for monitoring nerve function during a surgical procedure.

Referring to FIG. 4A, a method is disclosed for conducting a surgical procedure while monitoring nerve function. The surgical method is one that involves the use of a medical instrument that applies traction and/or compression, for example, that may result in damage of the nerves. However, the invention is not thereby limited, as the system disclosed herein can be used to monitor nerves under conditions not requiring of surgery. In situations when surgery is being performed, it is desirable to monitor such functioning of nerves to understand when an injury may be occurring and then perform a corrective action to avoid permanent injury to the nerves in the area of the surgery. According to the disclosed method, nerves that are proximal to the surgical site and distal to the surgical site are monitored to effectively test across the surgical site to provide a more sensitive method for determining the onset of any loss of nerve function at or in proximity to the surgical site, such as where a retractor may be placed. In addition to testing effectively across the surgical site in a proximal to distal and distal to proximal fashion, the method also employs testing various types of nerve fibers as well as testing the nerves in an orthodromic and antidromic manner. While FIG. 4A shows the nerves being monitored include the L2, L3, and L4 nerve roots, the method disclosed herein is not thereby limited. In FIG. 4B, for example, a method is disclosed for conducting a surgical procedure while monitoring nerve function that can include any one of the C1 to S5 nerve roots, all roots, trunks, divisions, cords, or branches of the brachial and lumbosacral plexus, and genitofemoral, lateral femoral cutaneous, femoral, and obturator nerves.

The method begins at block 400. From block 400, the method enters block 402. Block 402 is to designate that the probes at the nerve roots L2, L3, L4, the femoral nerve, the probes at the myotomes, and the probes at the dermatomes are in place from the subroutine described in association with FIG. 2. From block 402, the method enters block 404. In block 404, a medical instrument, such as a retractor, is either advanced, expanded, or held in place in the incision that was made in the subroutine described in association with FIG. 3, the localization procedure. The disclosed method provides an indication to the physician whether at any time during the use of the retractor, the onset of the loss of nerve function may be imminent. Nerve function may diminish when tissues are placed under traction or compression. Furthermore, loss of nerve function can also be time dependent. Accordingly, throughout the surgical procedure, the disclosed method continuously tests the various types of nerve fibers in different directions to provide the physician with more sensitive information regarding the loss of any nerve function. The sensory conduction study will typically show failure of the nerves first. The mixed conduction study will typically next show a failure of the nerves. The triggered EMG studies will typically show loss of nerve function last.

The retractor can be placed in the incision that was made earlier using the localization probe. As the physician advances and/or expands the retractor, or even when the retractor is held in place, stimulus signals are provided by a series of probes at various nerve locations and measured at other various nerve locations that are distal or proximal to the stimulus location. In essence, the signals are made to traverse across the surgical wound from the stimulation location to the response location. In this manner, the nerve function during surgery can be compared to the earlier baseline nerve function data collected when no surgical wound was present. The blocks 406-418 describe representative studies that may be performed to monitor the nerve function during the surgical procedure. The nerve studies defined by these blocks are the same ones that were earlier used to define the baseline waveforms. In block 406, a stimulus is provided at the distal femoral nerve and the response is measured and/or graphed at the proximal nerve roots L2, L3, and L4. In block 408, a stimulus is provided at the proximal nerve roots L2, L3, and L4, one at a time, and the nerve function response is measured and/or graphed at the distal femoral nerve. In block 410, a stimulus is provided at the distal dermatomes, one at a time, and the nerve response is measured and/or graphed at the proximal nerve roots L2, L3, and L4. In block 412, a stimulus is provided, one at a time, at each of the proximal nerve roots L2, L3, and L4 and the nerve function is measured and/or graphed at the distal dermatomes. In block 414, a stimulus is provided at the proximal nerve root L2 and the EMG response is measured and/or graphed at the distal myotome. In block 416, a stimulus is provided at the proximal nerve root L3 and the EMG response is measured and/or graphed at the distal myotome. In block 418, a stimulus is provided at the proximal nerve root L4 and the EMG response is measured and/or graphed at the distal myotome. The timing of the stimulus, to what probe the stimulus is provided, the voltage, amplitude, amperage, time delay, and duration of the stimulus signal, as well as reading and comparing the response to the baseline, can be under control of a neuromonitoring machine that will be described in more detail below. For example, amplitude and duration of the stimulus signal may increase in stepwise increments.

Each time a stimulus is provided in one of blocks 406-418 and a nerve or EMG response is obtained, the response is compared to the baseline waveform obtained from the method disclosed in FIG. 2. It is possible that a comparison of the nerve function response waveform to the baseline waveform will show one of four possibilities: (1) no change, (2) increased latency, (3) decreased amplitude, or (4) complete loss of the waveform. If no change is noticed, it means that the nerve is functioning properly, i.e., no differently than the baseline. If any of the other conditions are noticed, the system may provide a notification to the physician and timestamps the graph. The degree of change recognized in the various electrodiagnostic testing modes gives the surgeon an idea of "real time" nerve performance and gives indication of early nerve compromise. Examples of how a surgeon would utilize this information are various and dependent on each surgeon. For example, the following conditions may arise: (1) If the waveforms are unchanged from baseline even after the retractor is in place and expanded, then the surgeon can continue the procedure without change; (2) If the sensory waveforms begin to reveal deterioration once the retractor is placed and expanded, then the nerve(s) or neural structures are already under a certain amount of compression/traction and should be monitored closely for further deterioration; (3) If further deterioration occurs, then the retractor should be relaxed, reduced in size, and the procedure should be paused until the nerve performance has returned to baseline or within a reasonable limit from the baseline. Other actions may be possible, and the ones mentioned above should not be construed as the only possible actions to take. For example, the stimulus strength may increase or decrease, or other actions may be appropriate. Deterioration of the nerves will generally be realized by increased latency, meaning the time following a stimulus to the time a response is recorded increases, or by decreasing amplitude of the response. The retractor can then be expanded again and the surgery proceeds. It may be necessary to relax the retractor numerous times during the surgical procedure in order to ensure neural structure preservation. If the waveforms including sensory, motor, mixed, and triggered electromyography exhibit immediate deterioration to a point where there is no response to stimulus once the retractor is placed, a drastic change in surgical approach may be considered because the likelihood of significant neural injury is imminent.

During retractor placement and expansion, variable degrees of compression and traction will be placed on the various types of nerves. The disclosed method selects to test different nerves that can potentially show different rates of deterioration. The sensory conduction studies are represented in blocks 406, 410, 412, the mixed nerve conduction studies are represented in block 408, and the triggered EMGs are represented in blocks 414, 416, 418. The specific order (e.g., sensory>mixed>motor or motor>mixed>sensory) in which nerve performance is negatively affected by compression, traction, and/or vascular compromise can vary.

By providing the physician with information concerning the sensory, motor, and mixed nerves spanning across, around, or through the surgical site from proximal to distal, or distal to proximal, the physician will be able to assess whether any potential damage is being done to the nerve(s) or nerve structures and modify the surgical procedure, or approach as needed in order to preserve neural integrity and function.

FIG. 4B is similar to the method disclose in FIG. 4A; however, the nerves to be monitored include any nerves selected from one or more of the C1 to S5 nerve roots, all roots, trunks, divisions, cords, or branches of the brachial and lumbosacral plexus, genitofemeral, lateral femoral cutaneous, femoral and obturator nerves. All other steps of FIG. 4B are similar to the steps of FIG. 4A.

Next, the hardware used in conducting the above-mentioned studies will be described.

Figure 6:
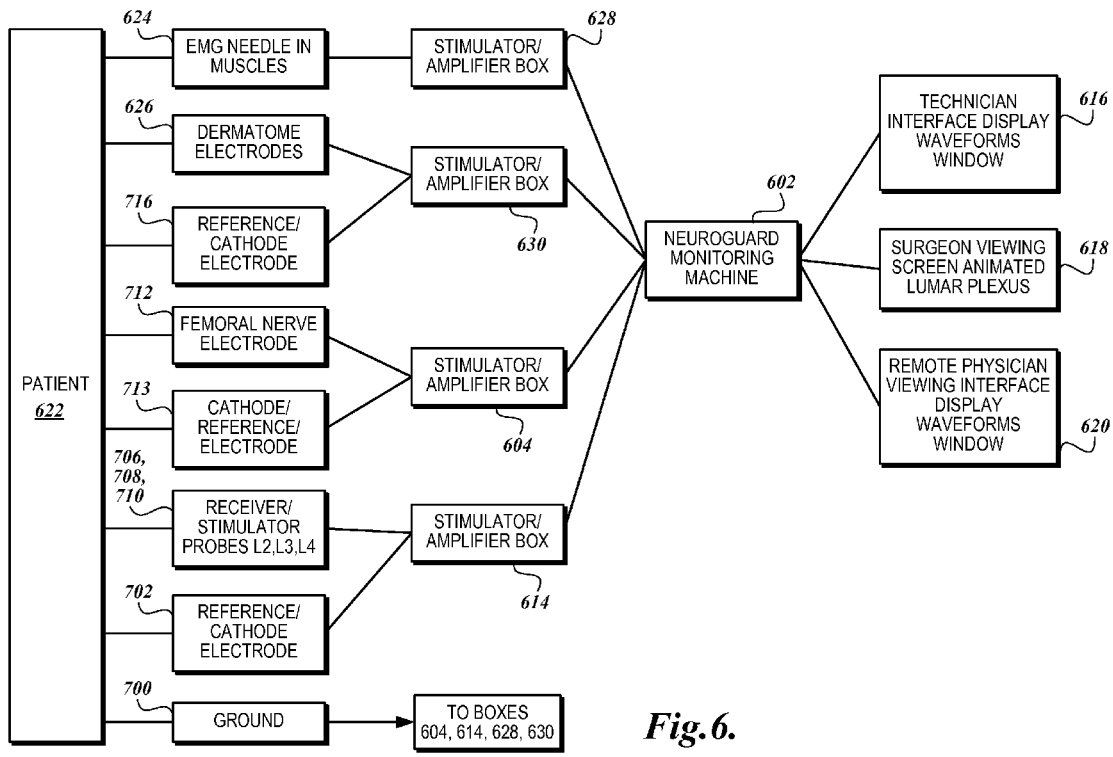
FIG. 6 is a diagrammatical illustration of a system used to monitor nerve function in accordance with one embodiment of the invention.

FIG. 6 is a diagrammatical illustration of a system for carrying out nerve conduction and EMG studies as described in association with FIGS. 2, 4A, and 4B.

The system includes the neuromonitoring machine 602. The function of the neuromonitoring machine 602 is, among others, for controlling the stimulus to each of the respective probes in a predetermined schedule. For instance, the voltage, amperage, frequency, and duration or pulse width of each stimulus can be controlled with the neuromonitoring machine 602. A suitable neuromonitoring machine that can be configured according to the disclosure herein is commercially available under the designation CASCADE manufactured by Cadwell Laboratories, Inc.

The suitable neuromonitoring machine 602 includes hardware and software capable of being programmed in accordance with the disclosed methods herein to generate an electrical stimulus, receive and process electrical signals generated by muscle or nerve tissues, and display in graphical form the response and compare the response signal to a baseline signal. Comparison can be by displaying both the baseline and current waveform simultaneously in real time, overlapping one another, or in different screens or sections of a screen. Further comparisons can be performed by the use of mathematical algorithms that can give an indication of the "closeness" of one waveform to another. The neuromonitoring machine 602 includes software and controls. For example, controls may be hard or soft controls, such as switches or dials. The controls allow the technician or physician to make various adjustments to the stimulus signal, and provide choices as to the probe or probes to use for the stimulus signal. Further, the controls can allow the technician or physician to customize a display window that shows the waveforms of the response signals. Additionally, well-known controls, such as brightness and contrast, can also be implemented in the neuromonitoring machine. Further, the communication between technician or physician and the neuromonitoring machine may be, by way of a graphical user interface or GUI, capable of communicating information. In addition, the neuromonitoring machine includes any additional accessories, software drivers and modules, and electrical components to connect to a stimulator/amplifier (slave box) and/or the various nerve and EMG or myotome or dermatome probes and electrodes. These additional components not specifically mentioned herein are apparent to those of skill in the art. The controls on the neuromonitoring machine will allow the technician or physician to control the stimulus intensity, the duration of the stimulus, and the frequency. The software of the neuromonitoring machine may allow the technician or physician to program the sequence and/or the stepwise increments of advancing any one of these variables. Further, the software may allow the technician or physician to adjust the sensitivity of the receiver probes to eliminate any interference or background noise.

The following nerve conduction and EMG studies are representative when performing lateral transpsoas surgery and should not be limited solely to the studies identified below. Nerve conduction studies 1 through 4 may be combined with electromyography studies 5 through 7.

1. An orthodromic sensory conduction study by applying a stimulus at the distal femoral nerve and measuring a response at proximal L2, L3, or L4 nerve roots. (Block 406.)
2. A mixed nerve conduction study by applying a stimulus to each one of the proximal nerve roots L2, L3, and L4, one at a time, and measuring a response at the distal femoral nerve. (Block 408.)
3. An orthodromic sensory conduction study by applying a stimulus to a distal dermatome and measuring the response at the corresponding proximal nerve root L2, L3, or L4. (Block 410.)
4. An antidromic sensory conduction study to provide a stimulus at a proximal nerve root L2, L3, and L4, one at a time, and measuring the response at the corresponding distal dermatome. (Block 412.)

5. Triggered electromyography (EMG) by providing a stimulus at the proximal L2 nerve root and measuring the response at the corresponding distal myotome. (Block 414.)
6. Triggered electromyography (EMG) by providing a stimulus at the proximal L3 nerve root and measuring the response at the corresponding distal myotome. (Block 416.)
7. Triggered electromyography (EMG) by providing a stimulus at the proximal L4 nerve root and measuring the response at the corresponding distal myotome. (Block 418.)

Both sensory and motor nerves can be monitored. Sensory and motor signals are generated and recorded in a similar manner, but stimulation and recording parameters may differ. A sensory conduction study may be performed with a series of stimulations, and then the responses are averaged. Averaging is performed when a generated signal is small in amplitude and other electrical signals, interference, or "background noise" is likely to dominate the recording. Averaging allows the elimination of this "background noise." A sensory nerve conduction study may have a stimulus intensity of 10-100 milliamps (mA), a duration of 0.02-0.07 milliseconds (ms), and a frequency of 3-6 Hz. A compound sensory nerve action potential recording, which may or may not be averaged, is usually recorded with a sensitivity setting of 10-100 microvolts (μV) amplitude, and 10-100 milliseconds (ms) timebase, and latency is measured to the peak of the waveform.

A motor nerve conduction study may have a low-frequency filter set at 30 Hz and a high-frequency filter set at 1 kHz settings, a stimulus intensity of 1-100 mA, a duration of 0.02-0.05 milliseconds, and a frequency of 1-5 Hz. A compound motor action potential response is usually recorded with a sensitivity setting of 10-20 millivolt (mV) amplitude, and 25-50 millisecond (ms) timebase, and latency is measured to the onset of the waveform.

Free run electromyography sensitivity is set at 50-500 microvolt (μV), low-frequency filter (LFF) 20-30 Hz, high-frequency filter 10 kilohertz (kHz) with a sweep speed of 10-200 millisecond (ms) per division.

Triggered electromyography settings may use a stimulus intensity of 0.1-3 milliamps (mA), a frequency of 1-3 Hz, a pulse width of 0.2 millisecond (ms) duration, a time base of 25-50 millisecond (ms) and a sensitivity set at 50-100 mV. All of the stimulus and recording parameters are variable for each individual case. The timebase will be dependent on the length of the segment of nerve being tested. The longer the segment of nerve being tested, the longer a timebase is required in which to capture the nerve or muscle response. Parameters may change for different patients and/or different procedures. The neuromonitoring machine 602 may also have an algorithm that decides which probes will receive a stimulus, based on feedback from the physician or the measured response.

The system includes one or more stimulator/amplifier boxes ("slave" boxes) that are connected to each probe where a stimulus will be provided and from which each response will be received. The system may include a plurality of such boxes to serve one or a group of probes in proximity to each other, or a single box to which all probes attach. As depicted in FIG. 6, the stimulator/amplifier boxes include 604, 614, 628, and 630. The stimulator/amplifier boxes include circuits to both provide a stimulus to the probe(s) and amplification circuits to amplify any signal detected by the probe(s) before sending to the neuromonitoring machine 602. In this regard, a probe can function to deliver a stimulus to a nerve in one study, and the same probe can be used to receive a response in another study. Furthermore, the stimulator/amplifier boxes may include a switch that allows the switching of the probe function from stimulus provider to response receiver. In one embodiment, the system includes probes 706, 708, and 710 for each of the nerve roots L2, L3, and L4, probe 712 for the femoral nerve, and probes 624 and 626 for the myotomes and dermatomes, respectively, corresponding to the L2, L3, and L4 nerve roots. The system includes additional electrodes connected to each stimulator/amplifier box to function as reference, ground, or cathode electrodes. Such additional electrode can function as a cathode when a probe is providing a stimulus or as a reference when a probe is providing a response. For example, the system includes a reference electrode 702 connected to the stimulator/amplifier box 614 to allow probes at L2, L3, and L4 nerve roots to function as receiver probes. The reference electrode is used to detect other non-vital electrical signals that may be conducting through or around the patient. These non-vital signals are carried to the amplifier box by the reference electrode and subtracted from the signal obtained via the recording probe (s)/electrode(s), which leaves the vital signal information intact to be sent back to the neuromonitoring machine 602 and converted into a waveform. Electrode 702 may function as a cathode when nerve root probes 706, 708, and 710 are functioning as simulation probes (anodes). Other reference/cathode electrodes include, for example, electrode 716 connected to stimulator/amplifier box 630 that is also connected to dermatome probes 626, and electrode 713 connected to stimulator/amplifier box 604 that is also connected to femoral nerve probe 712. A ground electrode 700 is connected to each of the simulator/amplifier boxes. For example, ground electrode 700 is connected to the stimulator/amplifier box 614 to allow probes at L2, L3, and L4 nerve roots to function as receiver probes. The ground electrode 612 is ideally an infinite source or sink for charge, which can absorb an unlimited amount of current without changing its potential. The system may include an interface 616.

The interface 616 may include displays to enable a technician to view the response, such as a waveform, from each receiver probe. The interface 616 may also have soft or hard controls to make remote adjustments to the neuromonitoring machine 602. The system may include a screen 618. The screen 618 may be used for displaying the localization of the lumbar plexus during the subroutine described in association with FIG. 3. The system may include a remote interface and/or display 620. The remote interface and/or display may provide the ability for remote control of the neuromonitoring machine 602. The remote interface 620 may also provide the capability to view the response waveforms. The neuromonitoring machine 602 communicates to and from the interface display 616, the screen 618, and the remote interface and display 620. Furthermore, the neuromonitoring machine 602 communicates to and from the one or more stimulator/amplifier boxes 604, 614, 628, and 630. As depicted in FIG. 6, the stimulator/amplifier box 604 communicates with the femoral nerve probe/electrode 712 or combination of electrodes that are either on the skin, or inserted deep to the skin over the femoral nerve. When functioning to provide a stimulus, the probe is considered an anode. Also connected to the stimulator/amplifier box 604 is a cathode electrode 713. When acting as anodes to provide electrical stimulation, a cathode electrode is placed in proximity to the probes.

Figure 7:
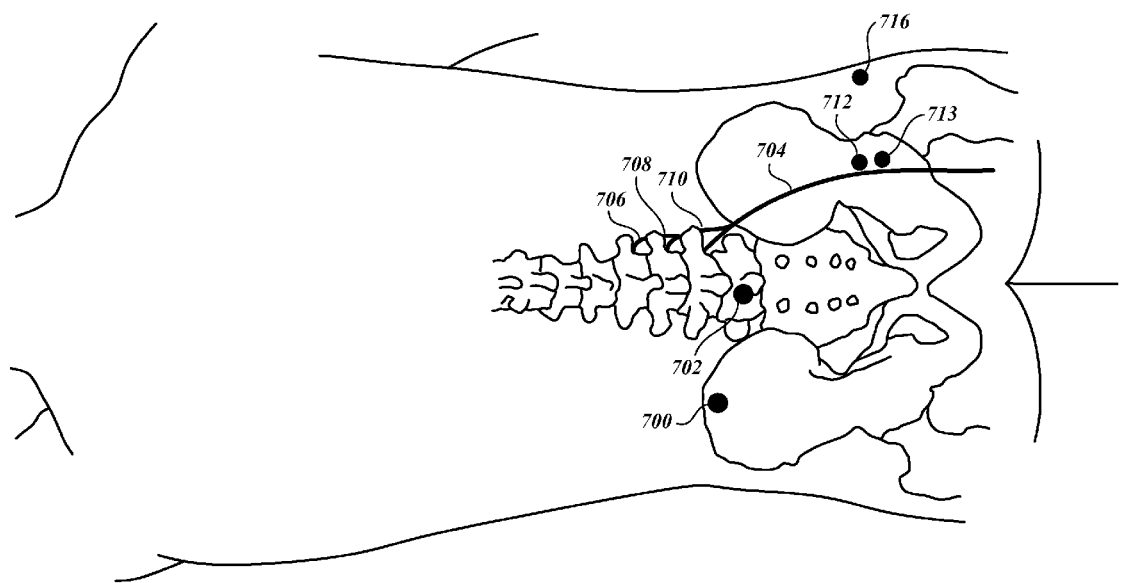
FIG. 7 is an illustration of nerve location and electrode placement to monitor nerve function in accordance with one embodiment of the invention.

FIG. 7 is a diagrammatical illustration of the location of the various nerves and probe placement that are disclosed for use in the nerve conduction studies specifically for the lateral transpsoas approach. Dermatome and myotome locations are not shown as these locations are apparent to those of skill in the art. The femoral nerve electrode 714 is positioned on or in the femoral nerve 704. Similarly, probes are placed at or in proximity to the nerve roots L2, L3, and L4, respectively, at locations 706, 708, and 710. The location of probes L2, L3, and L4 are proximal in relation to the surgical site of a lateral transpsoas approach, while the probe location 714 for the femoral nerve is distal. The placement of the probes at the femoral nerve and the L2, L3, and L4 nerve roots may use a probe as disclosed herein that is unlike probes that are currently in use. Probes are placed utilizing the procedure as disclosed above in connection with FIG. 5. Dermatome electrodes, depicted collectively as 626 in FIG. 6 are not shown in FIG. 7. However, the dermatome locations corresponding to the L1, L2, and L3 nerve roots are apparent to one skilled in the art. The EMG electrodes depicted collectively as 624 in FIG. 6 are not shown in FIG. 7. The muscles of the myotome locations include the psoas, vastus medialis, and rectus femoris. Electrodes suitable for dermatomes and myotomes in EMG studies are apparent to those skilled in the art.

In the orthodromic sensory conduction study (block 406), the distal femoral nerve probe 712, which is the anode to provide a stimulus, corresponds to location 712 in FIG. 7, and the electrode 713 is being used as a cathode and corresponds to location 713 in FIG. 7. Both probes connect to stimulator/amplifier box 604, shown in FIG. 6. The stimulator/amplifier box 604 uses a stimulator circuit, described in greater detail below, to send a stimulus signal to the femoral nerve probe 712. The proximal receiver probes for L2, L3, and L4 correspond to locations 706, 708, and 710 in FIG. 7, which connect to stimulator/amplifier box 614. To measure responses from receiver probes, a reference and ground electrode are required. To that end, the electrode 702 corresponds to location 702, and the electrode 700 corresponds to ground at location 700. Both electrodes 702 and 700 are connected to stimulator/amplifier box 614. The stimulator/amplifier box 614 uses a differential amplifier circuit, described in greater detail below, to determine the measured response from each of the nerve root probes. The L2, L3, and L4 probes are located deep so that the distal ends of the probe are in proximity to and/or touching the L2, L3, and L4 nerve roots exiting the neuroforamen. The reference electrode 702 is either on the skin or deep to the skin, and the ground electrode 700 is located on the skin. Orthodromic sensory conduction studies may result in waveforms capable of being shown on the display 616. A representative display may show, for example, various windows within one display. Orthodromic sensory conduction studies may be depicted in one window of the display. Each window showing waveforms may include tool bars or menus that allow the user to select various features that affect the display. A second window may display waveforms of free run electromyography, which can give indications when a nerve is actively being manipulated. Adjustments can be made to stimulus intensity, pulse width, frequency, filters, stored versus current waveforms, timebase, sensitivity, averaging. A third window may show user selectable options for conducting the different studies, such that previously performed studies or stored waveforms may be recalled and compared, different testing montages can be recalled, and windows can be manipulated and reduced in order for better visualization of the waveforms.

A system for performing a mixed nerve conduction study (block 408), for example, providing a stimulus to each one of the nerve roots L2, L3, and L4 individually and measuring the response at the femoral nerve, may use the same hardware as described above in connection with FIG. 6 and, therefore, will not be described again for brevity. However, in contrast to orthodromic sensory conduction studies, the operation of mixed nerve conduction studies requires providing a stimulus to each one of the nerve roots via probes 706, 708, and 710 one at a time, followed by measuring the response at the femoral nerve via the probe 712. Further, in this study, the stimulator/amplifier box 604 uses the electrode 713 as a reference electrode, and the stimulator/amplifier box 604 uses a differential amplifier circuit to determine the response at the femoral nerve electrode 712. The stimulator/amplifier box 614 uses a stimulator circuit because the nerve root probes are providing a stimulus. The electrode 702 now functions as the cathode electrode to the L2, L3 and L4 probes acting as anodes. The graphical displays on the interface 616 may instead display waveforms produced by the mixed nerve conduction studies and would be labeled accordingly. Similarly, controls and adjustments would be labeled for the study that is presently being performed.

A system for carrying out orthodromic sensory conduction studies (block 410), for example, from each one of the dermatomes, one at a time, to the nerve roots may use the same hardware as described in association with FIG. 6 and utilizes the dermatome electrodes 626 as stimulator probes. Dermatome locations corresponding to the L2, L3, and L4 nerve roots are well known to those of skill in the art. For example, from "Atlas of Human Anatomy," Frank H. Netter, M.D., Ciba-Geigy Corp., pub., plate 150, 1989. In this study, the stimulator/amplifier box 630 connected to the dermatome electrodes 626 may have a plurality of connection sites for each one of the dermatome probes. When operating as a stimulator probe, the use of a cathode probe is required. To that end, the stimulator/amplifier box 630 is also connected to electrode 716, which in this study is a cathode electrode. FIG. 7 illustrates that the electrode 716 is placed at iliac crest or other boney prominence of the pelvis. The nerve root probes 706, 708, and 710 function as receiver probes, and, therefore, the electrode 702 functions as a reference electrode. The orthodromic sensory study, dermatome to nerve root, tests the sensory fibers from their terminal points at the skin to the nerve root. This study has the potential to be the most sensitive study for assessing early neural compression, traction, or vascular insult. The graphical displays on the interface may instead display waveforms produced by the orthodromic sensory conduction studies and would be labeled accordingly. Similarly, controls and adjustments would be labeled for the study that is presently being performed.

A system for carrying out antidromic sensory conduction studies (block 412), for example, providing a stimulus at a nerve root and measuring the nerve response at the dermatomes may use the same hardware as described in association with FIG. 6. However, in contrast to the stimulus being provided at the dermatomes, the stimulus is provided at the nerve roots L2, L3, and L4 one at a time. This is considered antidromic because for sensory nerves, such as dermatomes, the normal direction is to conduct from the skin to the brain. This study tests in the opposite direction. The stimulator/amplifier box 614 uses electrode 702 as a cathode electrode when nerve root probes are anodes providing a stimulus. The dermatome electrodes are active to receive a response, and therefore, the electrode 716 functions as a reference electrode. The graphical displays on the interface 616 may instead display waveforms produced by the antidromic sensory conduction studies and would be labeled accordingly. Similarly, controls and adjustments would be labeled for the study that is presently being performed.

A system for carrying out L2 nerve root triggered electromyography (EMG) (block 414) may use the same hardware as described in association with FIG. 6 and utilizes the EMG needle at the myotome. Muscles, such as the Psoas, Quadriceps (which include vastus medialis, vastus intermedias, vastus lateralis, rectus femoris), and Adductor Group (which includes adductor brevis, adductor magnus, adductor longus, gracilis, pectinus) corresponding to the L2 nerve root, as well as any other muscles, may be used to measure the response. The hardware provides a stimulus at the L2 nerve root, and the response is measured with the EMG needle. A probe used as a reference can be located on a boney prominence close to the EMG needle. The graphical displays on the interface may instead display waveforms produced by electromyography and would be labeled accordingly. Similarly, controls and adjustments would be labeled for the study that is presently being performed.

A system for carrying out L3 nerve root triggered electromyography (EMG) (block 416) may use the same hardware as described in association with FIG. 6 and utilizes the EMG needle at the myotome Muscles, such as the Psoas, Quadriceps (which include vastus medialis, vastus intermedias, vastus lateralis, rectus femoris), and Adductor Group (which includes adductor brevis, adductor magnus, adductor longus, gracilis, pectinus) corresponding to the L3 nerve root, as well as any other muscles, may be used to measure the response. The hardware provides a stimulus at the L3 nerve root, and the response is measured with the EMG needle. The graphical displays on the interface may instead display waveforms produced by electromyography and would be labeled accordingly. Similarly, controls and adjustments would be labeled for the study that is presently being performed.

A system for carrying out L4 nerve root triggered electromyography (EMG) (block 418) may use the same hardware as described in association with FIG. 6 and utilizes the EMG needle at the myotome. Muscles, such as the Psoas, Quadriceps (which include vastus medialis, vastus intermedias, vastus lateralis, rectus femoris), and Adductor Group (which includes adductor brevis, adductor magnus, adductor longus, gracilis, pectinus) corresponding to the L4 nerve root, as well as any other muscles, may be used to measure the response. The hardware provides a stimulus at the L4 nerve root, and the response is measured with the EMG needle. The graphical displays on the interface may instead display waveforms produced by electromyography and would be labeled accordingly. Similarly, controls and adjustments would be labeled for the study that is presently being performed.

As can now be fully understood, a feature of the stimulator/amplifier boxes 604, 614, 628 and 630 is the capability to function as both stimulator and amplifier, depending on whether the study that is being performed is orthodromic or antidromic, conducting proximal to distal, or conducting distal to proximal. One electrode can function as both the reference and cathode electrode depending on whether a second electrode at the nerve location is being used to stimulate the nerve or to record a response from the nerve. To that end also, the stimulator/amplifier boxes 604, 614, 628 and 630 are provided with a stimulator circuit and differential amplifier circuit with capability of switching manually or automatically via control from the neuromonitoring machine 602. This capability is described in more detail below.

Figure 8:
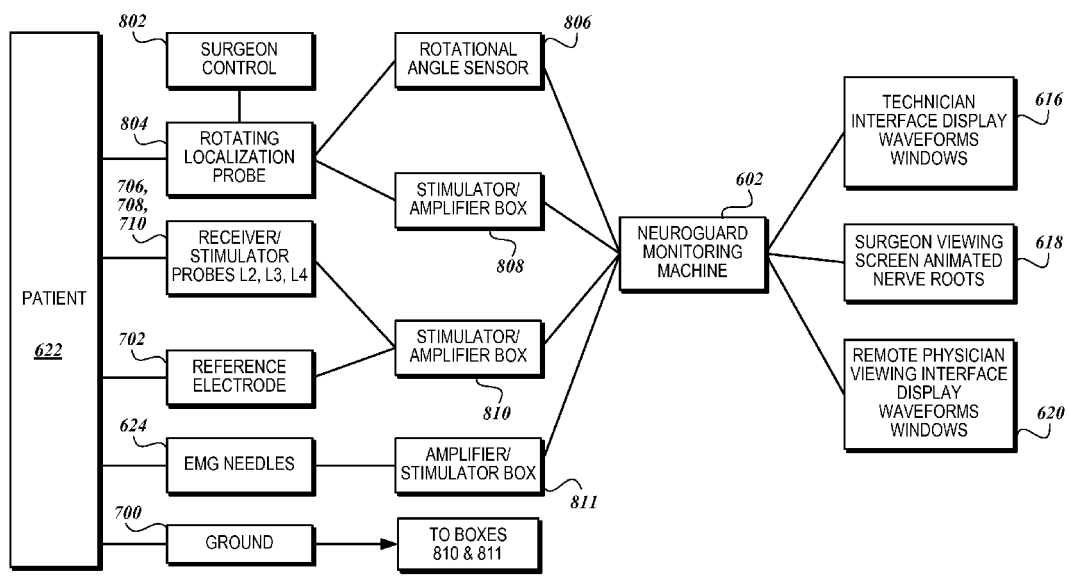
FIG. 8 is a diagrammatical illustration of a system for localizing a nerve in accordance with one embodiment of the invention.

FIG. 8 is a diagrammatical illustration of a system for carrying out the lumbar plexus localization technique that is described in association with FIG. 3. The system for this procedure includes some of the hardware described in association with FIG. 6, and, in addition, includes a localization probe 804 with a rotating tip that is described further below in association with FIGS. 11 and 12. In the configuration depicted in FIG. 8, the probes 706, 708, and 710 of the L2, L3, and L4 nerve roots, the EMG needles 624, and the electrode 702 can all connect to a single stimulator/amplifier box 810. The rotating localization probe 804 can connect to a stimulator/amplifier box 808. Simulator/amplifier boxes 808 and 810 can connect to the neuromonitoring machine 602. The stimulator/amplifier box 808 can send a stimulus signal to the distal tip of the localization probe 804. An outer sheath of the localization probe 804 can function as cathode, or, alternatively, an electrode dedicated to this purpose can be provided. A rotational angle sensor 806 keeps track of the distal tip position to allow determination of the direction of the unidirectional signal. The rotating probe 804 can provide a stimulus at a distal tip in a unidirectional manner that is only a few degrees (out of a total of 360) in width at the tip. When a unidirectional signal is provided by the tip, and depending on the nerve structure that is in the direction of the signal, the nerve can produce a response that is measured by the probes located at the nerve roots L2, L3, and L4, or the myotomes. The closer that the nerve structure is to the rotating probe tip, the stronger the response will be. For example, if the nerve is located on the opposite side of the probe to the active section of the probe tip, the response may initially be weak or unobtainable. The response would increase with every rotational adjustment that brings the active tip of the probe closer to the nerve. When the probe signal trajectory is directed towards the nerve (i.e., the closest point the probe is in relation to the nerve), the strongest response will be observed. As the probe is then rotated away from the nerve, the response will gradually diminish with each rotational adjustment. Rotation may include rotating the entirety of the probe or only the active tip. The localization probe 804 may include control means for allowing the surgeon to adjust the stimulus intensity, pulse width, depth, direction, and to rotate the probe manually or via a motorized synchronized system that records and analyzes all the data regarding stimulus and signal acquisition in order to generate a three dimensional image of the neural structure in the surrounding tissue. By keeping track of the probe rotation and depth of the probe tip in relation to a reference point and distance from the skin, the nerve or neural structure or structures that are to be avoided can be mapped with greater accuracy as compared when no reference point is used. These measurements can create a more accurate virtual image where radiologic images and anatomic measurements or markers are applied to the calculations of neural structure localization. A display can produce an animated version of the nerve, for example, showing in three dimension the location of the rotating probe with respect to any nerve.

Figure 9:
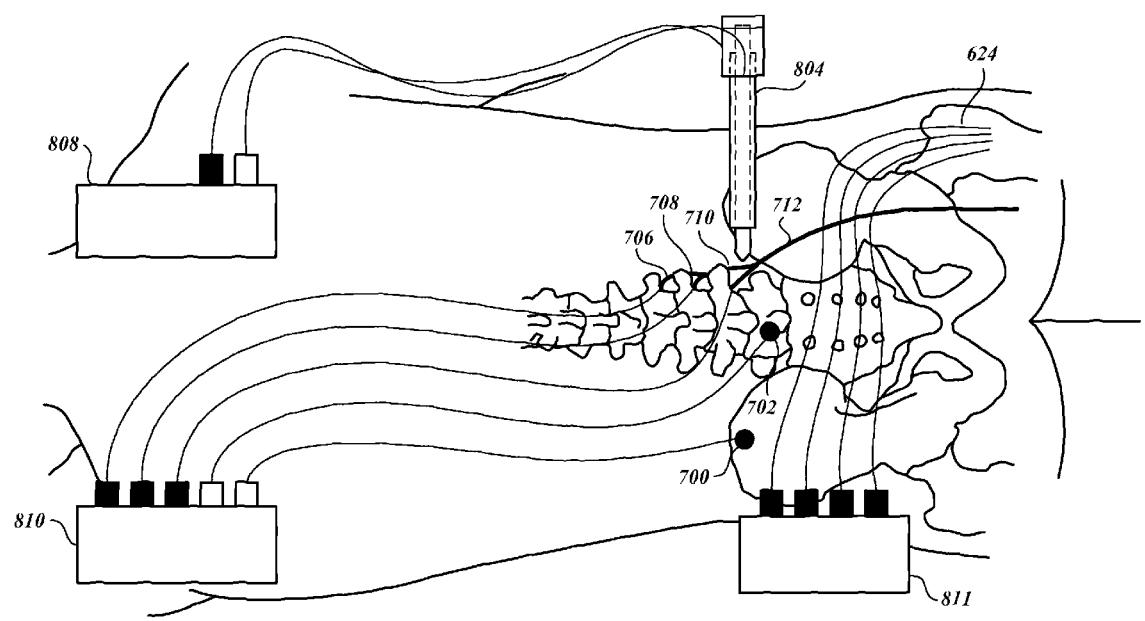
FIG. 9 is an illustration showing the nerve location and electrode placement for the procedure of localizing a nerve.

FIG. 9 is an illustration of the probe placement for the system described in association with FIG. 8. The rotating localization probe 804 is placed in the psoas muscle for lateral spinal access surgery. However, as mentioned above, the methods disclosed herein are not limited to any one particular surgery, the use of the psoas muscle for lateral spinal access surgery is merely mentioned as one representative example to illustrate the concepts disclosed. Similarly as with the nerve conduction studies and electromyography, the waveforms produced by the lumbar plexus localization study may also be displayed. A representative display may show, for example, simultaneously the responses at the L2, L3, and L4 nerve roots and triggered electromyography responses in the myotomes following a stimulus from the rotating probe 804. The waveforms detected at the femoral nerve may also be shown. The window showing the waveforms may include tool bars or menus that allow the user to select various features that affect the display. Adjustments can be made through the display through soft buttons to increase or decrease stimulus intensity, pulse width, frequency, filters, stored versus current waveforms, timebase, sensitivity, and averaging.

Figure 10:
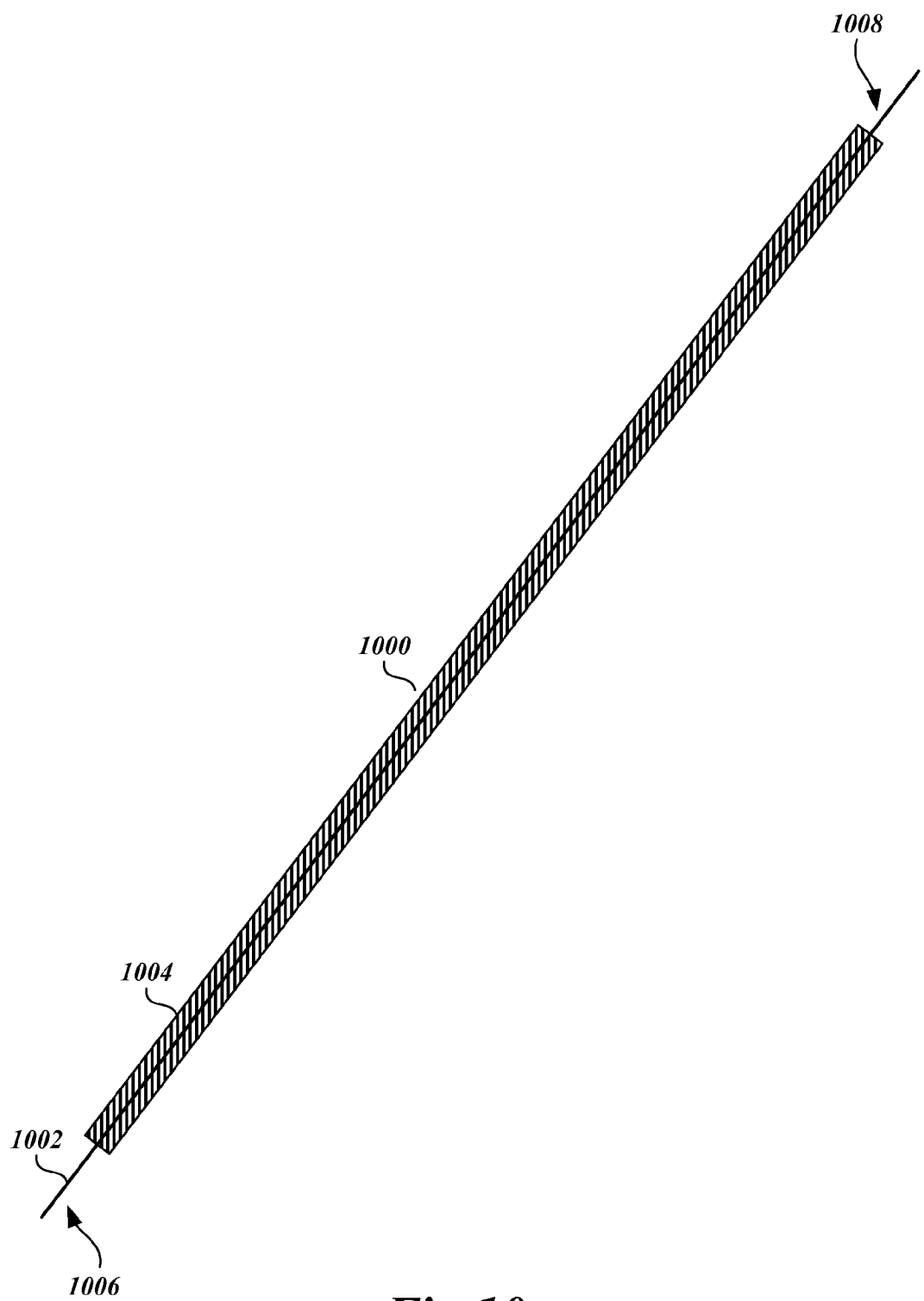
FIG. 10 is a diagrammatical illustration of an internal electrode for use in monitoring nerve function.

FIG. 10 is a diagrammatical illustration of a probe/electrode 1000 that can be used to access a nerve or neural structure that is deep to the skin in accordance with one embodiment of the present invention. This probe/electrode 1000 may be used for a variety of locations, including any of the spinal nerve roots L2, L3, L4, and femoral nerve or other neural structure mentioned herein. The nerve root probe/electrode 1000 includes insulated monofilament or braided electroconductive material that can be variable in caliber and length. The probe is made from a medical grade monofilament 1002 or braided wire coated with an electrical insulator 1004 with one or more exposed active points at the internal (distal) end 1006 and at the external (proximal) end 1008. In one embodiment, the probe is a 27 gauge, 8 inch medical grade monofilament wire (stainless steel) with insulation and 2 mm exposed ends. For this particular embodiment, an 18 gauge, 3.5 inch introducer needle can be used to place the probe 1000 at the desired location. In one embodiment, each active point can function independently as a stimulator or receiver site, or as an anode or cathode. The probe is of adequate caliber and resistance to neural structures with minimal degradation of signal. The probe is flexible and pliable, which allows the external portion of the probe to lie flush to the skin. The tip is blunt to avoid piercing a nerve, nerve sheath, thecal sack, or vascular structures. A coupler connects the external (proximal) end 1008 of the probe 1000 to a lead from an stimulator/amplifier box.

Figure 11:
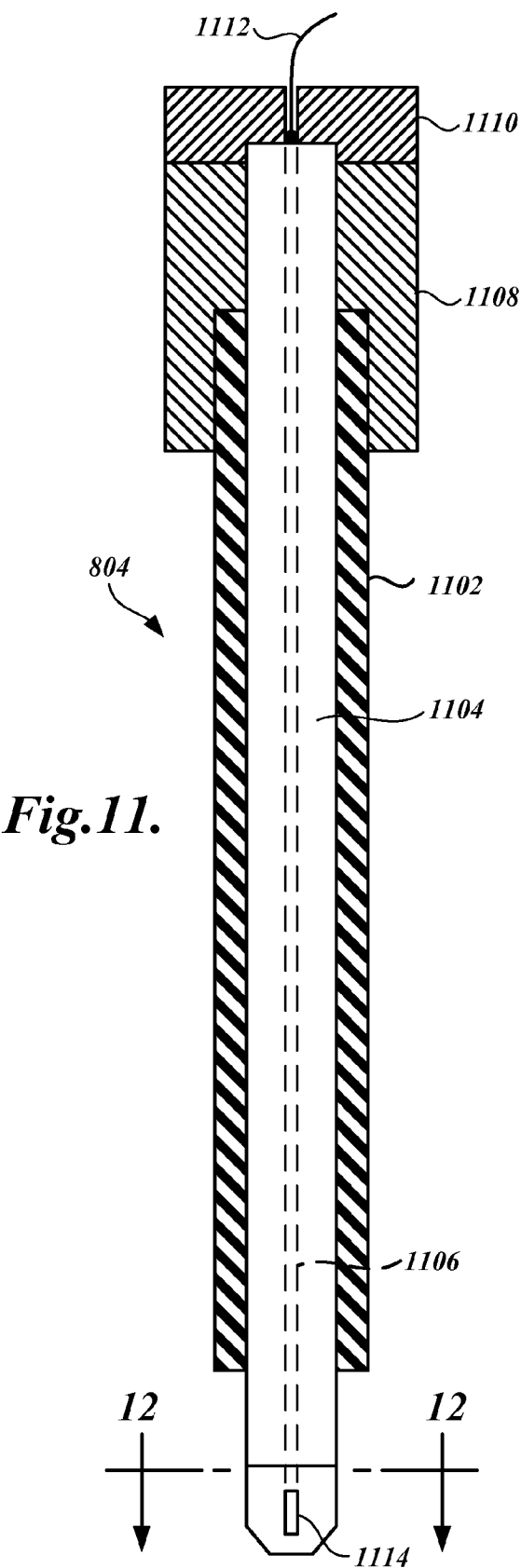
FIG. 11 is a diagrammatical illustration of a rotating electrode for sending a unidirectional signal.
Figure 12:
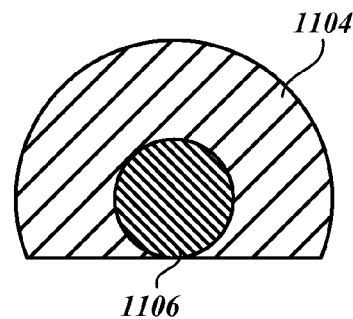
FIG. 12 is a diagrammatical illustration of a cross section of the electrode of FIG. 11 of the stimulator portion of a slave box.

Referring to FIG. 11, a stimulator probe 804 used in the localization subroutine of FIG. 3 is illustrated. The probe 804 includes an upper proximal body 1108. The body 1108 is connected to an exterior insulator or sheath 1102 that runs substantially the length of the probe except for terminating before the distal end. In one embodiment, the sheath may be conductive to function as a cathode. Interior to and juxtaposed next to the sheath 1102 is an insulator material 1104. The second insulator 1104 is configured to rotate within the sheath 1102. To that end, the insulator 1104 may be connected to a rotating wheel 1110 at a top end thereof. The wheel 1110 may be mechanically rotated or by hand. A magnetic switch or series of switches can be provided on the wheel 1110 that electrically convey the degrees of rotation of the wheel to a fixed reference point. Within the interior of the insulator 1104, an electroconductive material 1106 is provided that also rotates together with the insulator 1104. As seen in the cross sectional illustration of the tip in FIG. 12, the electroconductive material 1106 is not insulated on a side thereof at the distal (interior) tip of the probe 804 to leave a small exposed surface 1114 of the electroconductive material 1106 on one side only. In this manner, the stimulus signal can be sent only from the exposed surface 1114. This produces a unidirectional signal of several degrees of arc. The localization probe 804 is connected to a stimulator/amplifier box 808, and a stimulus is sent through the probe 804 as it is being inserted. The position indicator of the wheel 1110 is to indicate the direction in which the exposed electroconductive metal surface 1114 is directed. The direction may be represented graphically on a screen of the display 618 (FIG. 6). In one embodiment, the sheath can include incremental measurements to indicate the depth of the tip. Alternatively, depth can be measured through the use of sensors positioned along the length of the probe 804. In one embodiment, the rotating wheel 1110 of the probe is motorized, while in another embodiment, the rotation is manually controlled by the surgeon. The motor is connected to the wheel 1110 of the probe 804 so that as the motor rotates, the tip rotates at the same or different speed as the motor. The position can be reported in degrees such as from 0° to 360°. This information is synchronized and correlated with the electrical signals received by the nerve probes. This is particularly useful to allow mapping the location of a nerve.

FIGS. 13 through 16 schematically illustrate one embodiment of a stimulator/amplifier (slave box) apparatus 1200 for use in the methods disclosed herein. The slave box 1200 can be the slave boxes shown in the FIGURES as any one of elements 604, 614, 628, 630, 808, 810, and 811.

Figure 13:
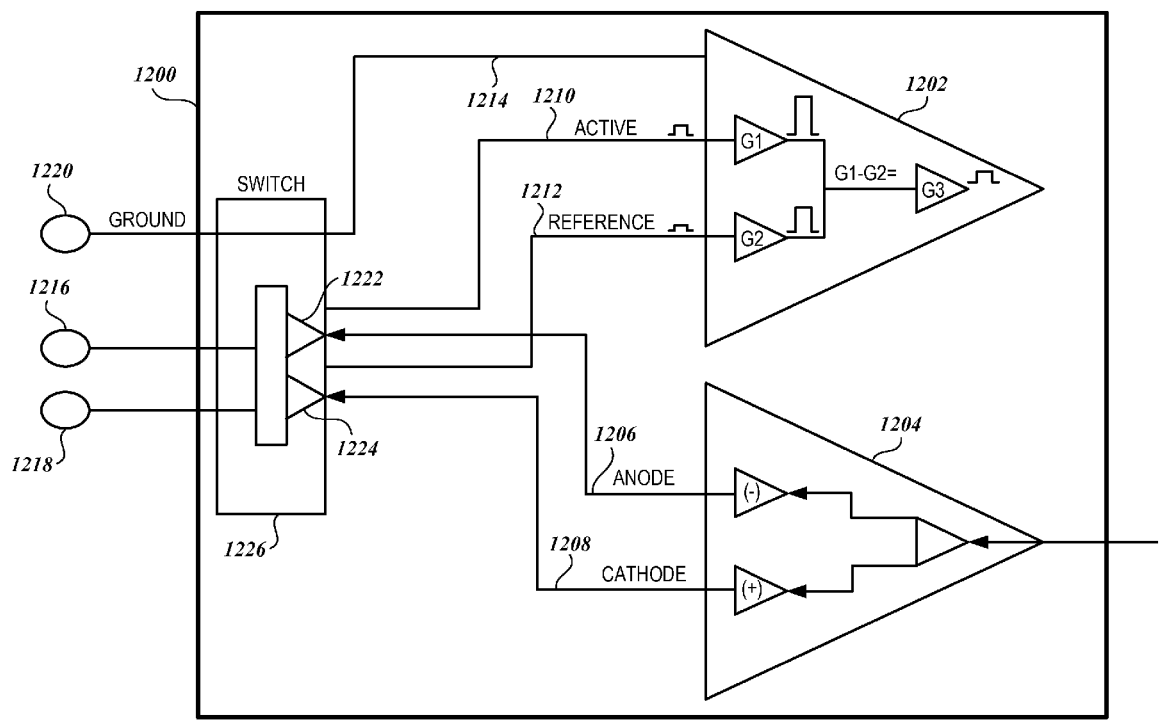
FIG. 13 is a diagrammatical schematic of a slave box with switching capability between the differential amplifier circuit and the stimulator circuit being switched to the stimulator circuit.

FIG. 13 is a diagrammatical schematic of a slave box 1200 including both the stimulator circuit 1204 and differential amplifier circuit 1202. The stimulator circuit 1204 has contacts 1206, 1208 for two probes, the anode and cathode, respectively. However, additional contacts can be added to allow using multiple probes. The stimulator circuit 1204 includes a circuit path connecting the anode 1206 and cathode 1208, wherein the anode 1206 receives the electric stimulus signal from the neuromonitoring machine described above.

The differential amplifier circuit 1202 includes contacts for three probes, active 1210, reference 1212, and ground 1214 probes. However, additional contacts can be added to have multiple active probes. More than one active probe can use the same ground and reference probes. The differential amplifier circuit 1202 measures the received signal at the active probe 1210, and measures the signal at the reference probe 1212, after signal conditioning and amplification, a differential signal is calculated and sent to the neuromonitoring machine. The differential signal is calculated from subtracting the signal measured using the reference probe from the signal measured using the active probe. A ground probe 1220 is connectable to the differential amplifier circuit 1202 of the slave box 1200. A first 1216 and a second 1218 probe are connectable to the switch 1226 on a first contact side thereof. The first probe 1216 can be an anode (stimulator) or active (receiver) probe, depending on switch 1226 position. The second probe 1218 can be a cathode or reference probe depending on switch 1226 position. The opposite contact side of the switch 1226 has a pair of contacts 1222, 1224 that are selectable to connect with either the anode 1206 and cathode 1208 contacts of the stimulator circuit 1204 or to the active 1210 and reference 1212 contacts of the differential amplifier circuit 1202. In a first switch position as shown in FIG. 13, the switch contact 1222 is making contact at the anode 1206 of the stimulator circuit 1204. The second switch contact 1224 is making contact with the cathode 1208 of the stimulator circuit 1204. In this mode, the electrode 1216 is the anode, and the electrode 1218 is the cathode.

Figure 14:
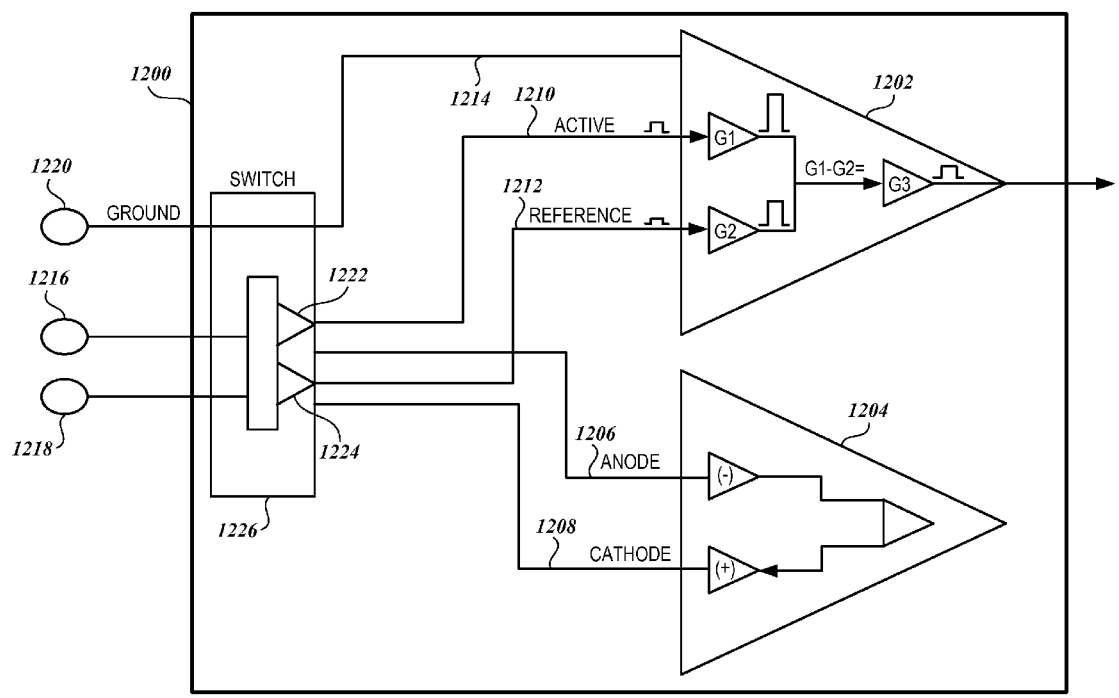
FIG. 14 is a diagrammatical schematic of the slave box with switching capability between the differential amplifier circuit and the stimulator circuit being switched to the differential amplifier circuit.

Referring to FIG. 14, the switch 1226 is shown in a second position. The pair of contacts 1222, 1224 on the switch 1226 are now aligned to the active 1210 and reference 1212 contacts of the differential amplifier circuit 1202. In this mode, the first electrode 1216 is the active probe, and the second electrode 1218 is the reference probe.

Figure 15:
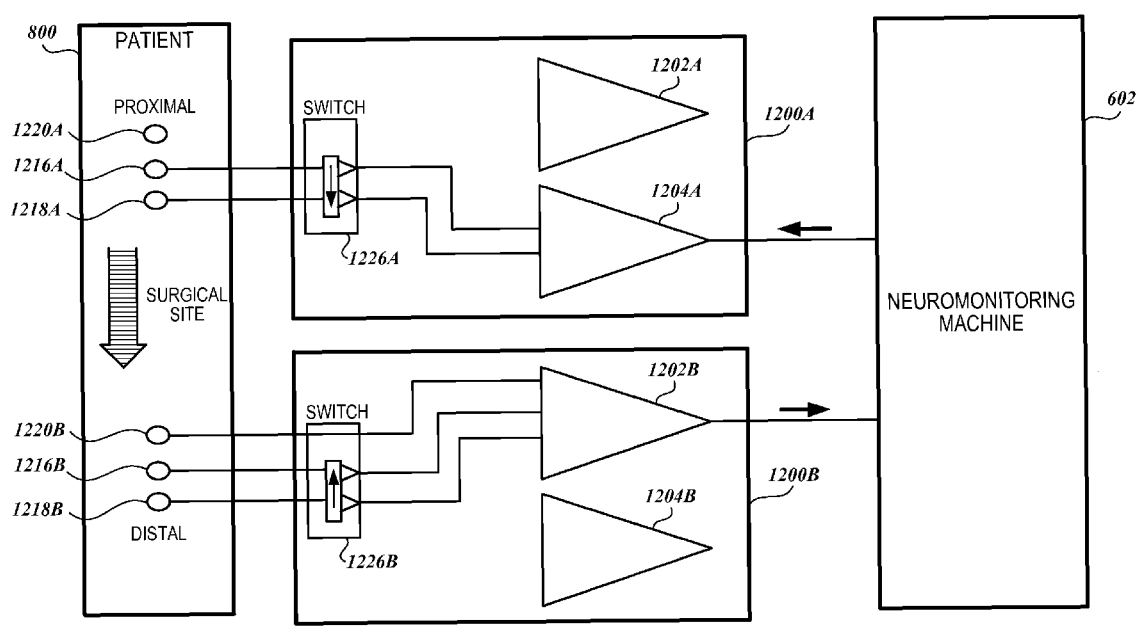
FIG. 15 is a diagrammatical schematic of two slave boxes connected to a neuromonitoring machine and a patient for performing a neurodiagnostic test from proximal to distal electrodes.

Referring to FIG. 15, a diagrammatical schematic of the slave box is shown for a representative proximal to distal nerve conduction study or triggered EMG study.

Figure 16:
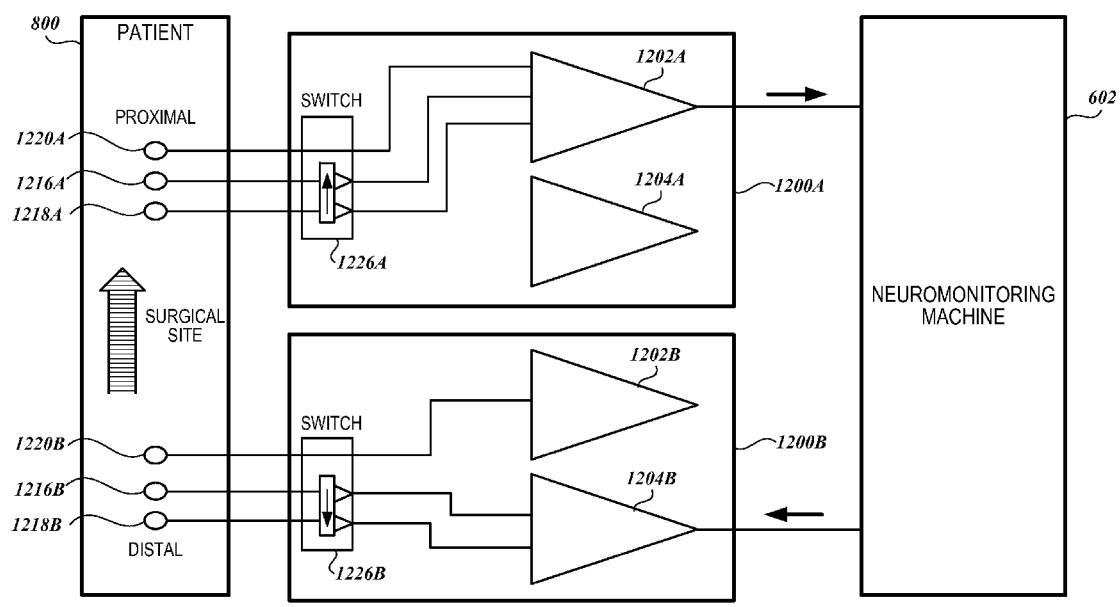
FIG. 16 is a diagrammatical schematic of two slave boxes connected to a neuromonitoring machine and a patient for performing a neurodiagnostic test from distal to proximal electrodes.

In this configuration, the neuromonitoring machine 602 is connected to a first 1200A and second 1200B slave box. The first slave box 1200A is connected to three or more electrodes 1220A, 1216A, and 1218A on the patient 800 at a proximal location in relation to a surgical site. The second slave box 1200B is connected to three or more electrodes 1220B, 1216B, and 1218B on the patient 800 at a distal location in relation to a surgical site. One electrode out of the three for each slave box 1200A, 1200B is a ground electrode, which in this case are represented by electrodes 1220A and 1220B. The two electrodes that are not the ground electrode function as a pair, such as the active and reference or the anode and cathode, depending on the switch position of the slave box. For example, in conducting proximal to distal, the first proximal slave box 1200A has the switch 1226A set to connect the anode contact of the stimulator circuit 1204A to a first proximal electrode 1216A and the cathode contact of the stimulator circuit 1204A to the second proximal electrode 1218A. In this mode, the first electrode 1216A is stimulating the nerve at a location proximal to the surgical site. In the second distal slave box 1200B, the switch 1226B is shown so that the active contact of the differential amplifier circuit 1202B is connected to the first distal probe 1216B and the reference contact of the differential amplifier circuit 1202B is connected to the second distal electrode 1218B. The neuromonitoring machine 602 can then send a stimulus at the proximal anode electrode 1216A and receive the response at the distal active electrode 1216B, thus allowing proximal to distal nerve conduction or EMG studies. FIG. 16 is provided to illustrate conducting distal to proximal nerve conduction studies using the same hardware as shown in FIG. 15 by operating the switches 1226A, 1226B on the respective first and second slave boxes 1200A, 1200B to a second position. The first distal electrode 1216B of the distal slave box 1200B can then be connected to the anode contact of the stimulator circuit 1204B, and the second distal electrode 1218B is connected to the cathode contact of the stimulator circuit 1204B. The first proximal electrode 1216A of the proximal slave box 1200A can then be connected to the active contact of the differential amplifier circuit 1202A, and the second proximal electrode 1218A is connected to the reference contact of the differential amplifier circuit 1202A. As can be seen, a proximal electrode can be used in proximal to distal nerve conduction or EMG studies as a proximal stimulator electrode, and the same proximal electrode can be used as an active receiver electrode in distal to proximal nerve conduction studies. Similarly, a distal electrode can be used in distal to proximal nerve conduction studies as a distal stimulator electrode, and the same distal electrode can be used as an active receiver electrode in proximal to distal nerve conduction studies. This advantageously allows for testing to be conducted from proximal to distal and from distal to proximal by the operation of a switch and without disconnecting and reconnecting the probes. Furthermore, the switches 1226A, 1226B can be hard wired switches or soft switches. In a hard wired switch, the physician or other surgical team member may physically move the position of the switch. Alternatively, the switches 1226A, 1226B can be "soft" switches and are controlled by software running on the neuromonitoring machine 602. Since the neuromonitoring machine 602 can select the nerve conduction study or EMG to execute, the neuromonitoring machine 602 can select the switch position as part of executing the nerve conduction study or EMG.

Figures 17A, 17B:
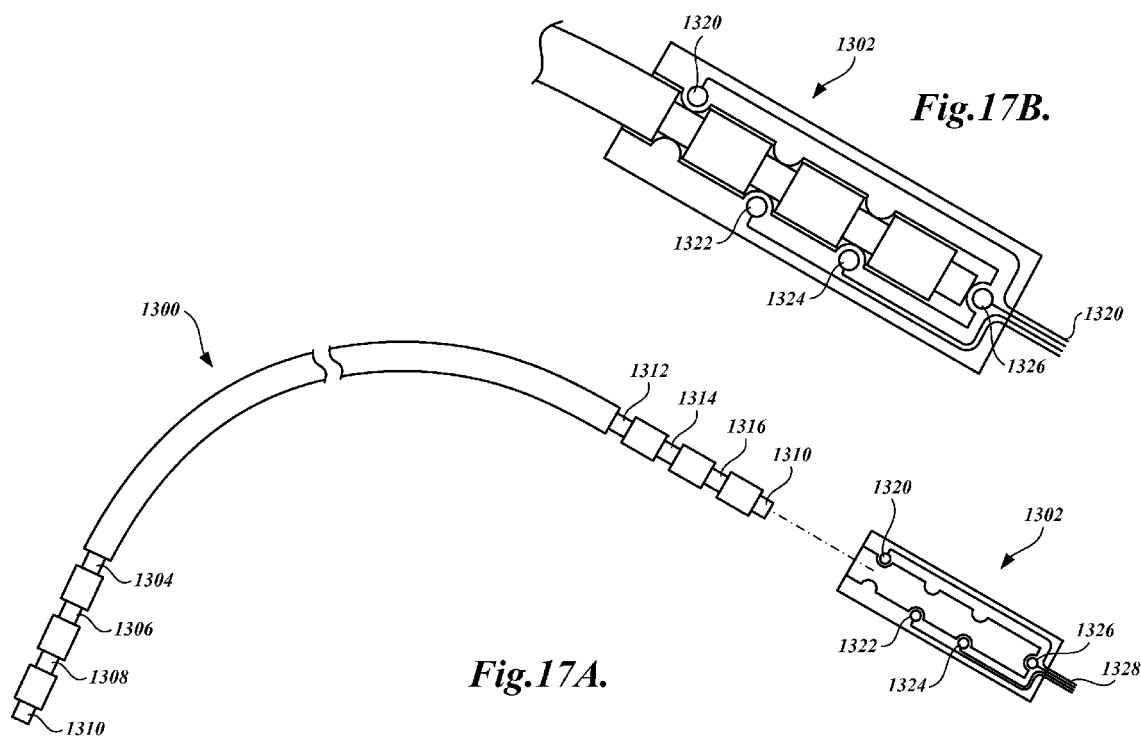
FIGS. 17A and 17B are diagrammatical illustrations of a multipoint electrode and coupler.

FIG. 17 is a diagrammatical illustration of a flexible, multiple point electrode 1300 and a corresponding coupling 1302. To render an electrode 1300 with multiple active points, the insulation can be stripped in a circumferential manner from several locations proximal to the distal tip end of the electrode 1300 shown as the active locations 1304, 1306, 1308, and 1310. For example, a multistrand conductor having four independently insulated wires can allow for four active points. Insulation can be stripped at the internal or distal tip to create the multiple active points 1304, 1306, 1308, and 1310 at the distal tip. Stripping the insulation from each independently insulated wire at a different location exposes the conductive material from the wire at a different point to serve as one of multiple active points of the probe. Similarly, corresponding points 1312, 1314, 1316, and 1318 at the external or proximal tip are created that allows connection to an stimulator/amplifier box via the coupling 1302. A representative coupling 1302 is illustrated alongside the electrode 1300. A female coupling 1302 having four independent connection sites 1320, 1322, 1324, and 1326 are each connected to a separate wire and then combined into an insulated multistrand conductor 1328 leaving the coupling 1302. The insulated multistrand conductor can be coupled to any stimulator/amplifier box. Each of the points of the external tip of the multipoint electrode are insulated from each other at both the external tip and the internal tip. For example, the probe can include multiple insulated wires wherein each insulated wire is stripped without stripping the other wires at the same location.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A system for monitoring neural function of a nerve, comprising:
   a first electrode configured to be suitable for nerve stimulus delivery and nerve response recordation;
   a first slave box connected to the first electrode, the slave box further comprising electrical stimulus circuitry and amplification circuitry to either deliver a stimulus to the first electrode via the stimulus circuitry or to receive a response from the first electrode via the amplification circuitry;
   a first switch having a first position to connect the first electrode to the electrical stimulus circuitry and disconnect the first electrode from the amplification circuitry to allow delivery of a nerve stimulus at the first electrode, and a second position to connect the first electrode to the amplification circuitry and disconnect the first electrode from the electrical stimulus circuitry to allow recording a nerve response at the first electrode; and
   a second electrode attached to the slave box, wherein the switch in the second position connects the second electrode to the electrical stimulus circuitry and disconnects the second electrode from the amplification circuitry, and the switch in the first position connects the second electrode to the amplification circuitry and disconnects the second electrode from the electrical circuitry.

2. The system of claim 1, wherein the switch is a hard wired switch or a software switch.

3. The system of claim 1, further comprising a neuromonitoring machine that controls the connection of the first electrode to the stimulus circuitry and to the amplification circuitry.

4. The system of claim 1, comprising a hard switch that controls the connection of the first electrode to the stimulus circuitry and the amplification circuitry.

5. The system of claim 1, further comprising a ground electrode connected to the amplification circuitry.

6. The system of claim 1, wherein in the first switch position the first electrode is connected to an anode in the stimulus circuitry, and the switch in the second position connects the first electrode to an active contact in the amplification circuitry.

7. The system of claim 1, wherein the amplification circuitry comprises differential amplification circuitry.

8. The system of claim 1, wherein the system further comprises a neuromonitoring machine configured to automatically connect the first electrode to the electrical stimulus circuitry, and automatically connect the first electrode to the amplification circuitry.

9. The system of claim 8, further comprising a second electrode configured to be suitable for nerve stimulus delivery and nerve response recordation;
> a second slave box connected to the second electrode, the second slave box further comprising second electrical stimulus circuitry and second amplification circuitry to either deliver a stimulus to the second electrode via the second stimulus circuitry or to receive a response from the second electrode via the second amplification circuitry;
> and a second switch having a first position to connect the second electrode to the second electrical stimulus circuitry and disconnect the second electrode from the second amplification circuitry to allow delivery of a nerve stimulus at the second electrode, and a second position to connect the second electrode to the second amplification circuitry and disconnect the second electrode from the second electrical stimulus circuitry to allow recording a nerve response at the second electrode, and the neuromonitoring machine is configured to automatically connect the second electrode to the amplification circuitry of the second slave box when the first electrode is connected to the electrical stimulus circuitry of the first slave box, and to automatically connect the second electrode to the electrical stimulus circuitry of the second slave box when the first electrode is connected to the amplification circuitry of the first slave box.

10. The system of claim 1, further comprising an electrode with a plurality of independent contacts at a distal tip of the electrode, wherein the electrode is electrically coupled to the slave box, and each of the contacts is provided at a different location of the electrode.

11. The system of claim 9, further comprising a third electrode connected to the first slave box and a fourth electrode connected to the second slave box, wherein the first switch is in the first position and connects the first and third electrodes to the electrical stimulus circuitry of the first slave box, and the second switch is in the second position and connects the second and fourth electrodes to the amplification circuitry of the second slave box.

12. The system of claim 9, further comprising a third electrode connected to the first slave box and a fourth electrode connected to the second slave box, wherein the first switch is in the second position and connects the first and third electrodes to the amplification circuitry of the first slave box, and the second switch is in the first position and connects the second and fourth electrodes to the electrical stimulus circuitry of the second slave box.

13. The system of claim 1, further comprising a third electrode connected to the slave box, wherein the switch being in the first position connects the third electrode to the electrical stimulus circuitry and disconnects the third electrode from the amplification circuitry, and the switch being in the second position connects the third electrode to the amplification circuitry and disconnects the third electrode from the electrical stimulus circuitry.

14. The system of claim 13, wherein the electrical stimulus circuitry comprises a cathode and anode, and the switch being in the first position connects the first electrode to the cathode and the second electrode to the anode.

15. The system of claim 13, wherein the amplification circuitry includes a reference contact and an active contact, and the switch being in the second position connects the first electrode to the reference contact and the second electrode to the active contact.

16. The system of claim 1, further comprising a second electrode configured to be suitable for nerve stimulus delivery and nerve response recordation;
> a second slave box connected to the second electrode, the second slave box further comprising second electrical stimulus circuitry and second amplification circuitry to either deliver a stimulus to the second electrode via the second stimulus circuitry or to receive a response from the second electrode via the second amplification circuitry;
> and a second switch having a first position to connect the second electrode to the second electrical stimulus circuitry and disconnect the second electrode from the second amplification circuitry to allow delivery of a nerve stimulus at the second electrode, and a second position to connect the second electrode to the second amplification circuitry and disconnect the second electrode from the second electrical stimulus circuitry to allow recording a nerve response at the second electrode.

17. The system of claim 16, further comprising a third electrode connected to the first slave box and a fourth electrode connected to the second slave box, wherein the first switch is in the first position and connects the first and third electrodes to the electrical stimulus circuitry of the first slave box, and the second switch is in the second position and connects the second and fourth electrodes to the amplification circuitry of the second slave box.

18. The system of claim 16, further comprising a third electrode connected to the first slave box and a fourth electrode connected to the second slave box, wherein the first switch is in the second position and connects the first and third electrodes to the amplification circuitry of the first slave box, and the second switch is in the first position and connects the second and fourth electrodes to the electrical stimulus circuitry of the second slave box.

* * * * *